(12) United States Patent
Teitelbaum et al.

(10) Patent No.: US 8,268,009 B2
(45) Date of Patent: *Sep. 18, 2012

(54) MECHANICAL EXTENSION IMPLANTS FOR SHORT BOWEL SYNDROME

(75) Inventors: Daniel H. Teitelbaum, Ann Arbor, MI (US); Jonathan E. Luntz, Ann Arbor, MI (US); Ariel U. Spencer, Jonesborough, TN (US); Diann E. Brei, Milford, MI (US); Brent A. Utter, Ann Arbor, MI (US); Joseph T. Belter, Novi, MI (US); Jennifer L. Vermeesch, Okemos, MI (US); Alexander D. Farr, Encino, CA (US); Makram P. Debbas, Clovis, CA (US)

(73) Assignee: The Regents of The University of Michigan, Ann Arbor, MI (US)

( * ) Notice: Subject to any disclaimer, the term of this patent is extended or adjusted under 35 U.S.C. 154(b) by 349 days.

This patent is subject to a terminal disclaimer.

(21) Appl. No.: 12/420,995

(22) Filed: Apr. 9, 2009

(65) Prior Publication Data

US 2009/0240339 A1 Sep. 24, 2009

Related U.S. Application Data

(63) Continuation-in-part of application No. 11/673,193, filed on Feb. 9, 2007, now Pat. No. 7,722,560.

(60) Provisional application No. 61/043,549, filed on Apr. 9, 2008.

(51) Int. Cl.
*A61F 2/04* (2006.01)
*A61F 2/00* (2006.01)
*A61M 29/00* (2006.01)

(52) U.S. Cl. ............... 623/23.64; 604/106; 604/107; 600/29; 600/37

(58) Field of Classification Search .............. 623/23.64; 604/106, 107; 600/29, 37
See application file for complete search history.

(56) References Cited

U.S. PATENT DOCUMENTS

| | | | |
|---|---|---|---|
| 5,415,660 A * | 5/1995 | Campbell et al. | 606/62 |
| 6,375,638 B2 * | 4/2002 | Nason et al. | 604/132 |
| 2005/0010191 A1 * | 1/2005 | Skinner et al. | 604/500 |
| 2006/0079897 A1 * | 4/2006 | Harrison et al. | 606/61 |

* cited by examiner

*Primary Examiner* — David H Willse
*Assistant Examiner* — Javier Blanco
(74) *Attorney, Agent, or Firm* — Harness, Dickey & Pierce, P.L.C.

(57) ABSTRACT

A bowel extension device implantable into a body for treatment of short bowel syndrome. The bowel extension device comprises a housing and a displaceable member coupled to the housing. The bowel extension device is configured to apply a tensile force sufficient to promote bowel growth without causing damage to the bowel. In some embodiments, the bowel extension device can be completely contained with the body.

8 Claims, 15 Drawing Sheets

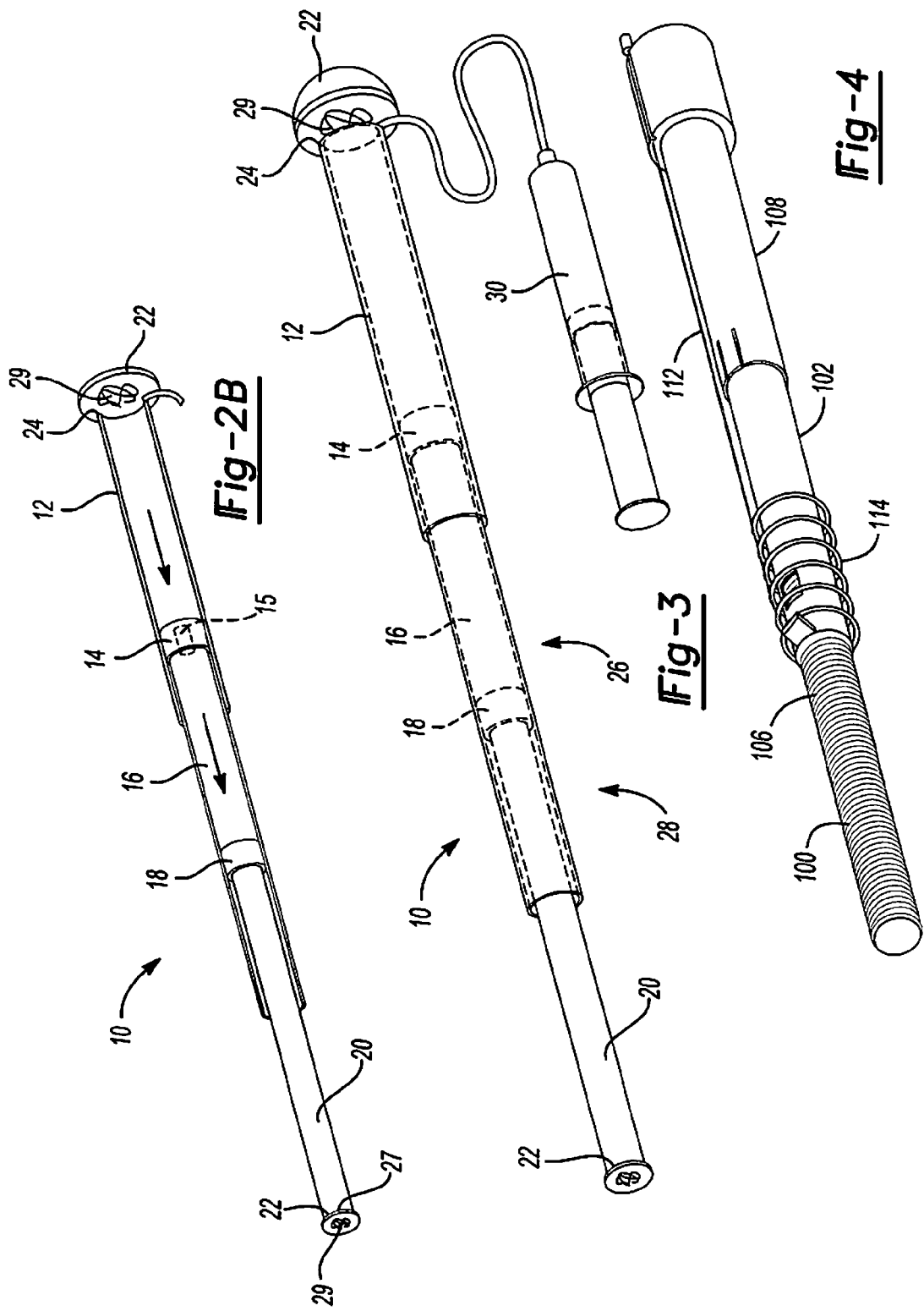

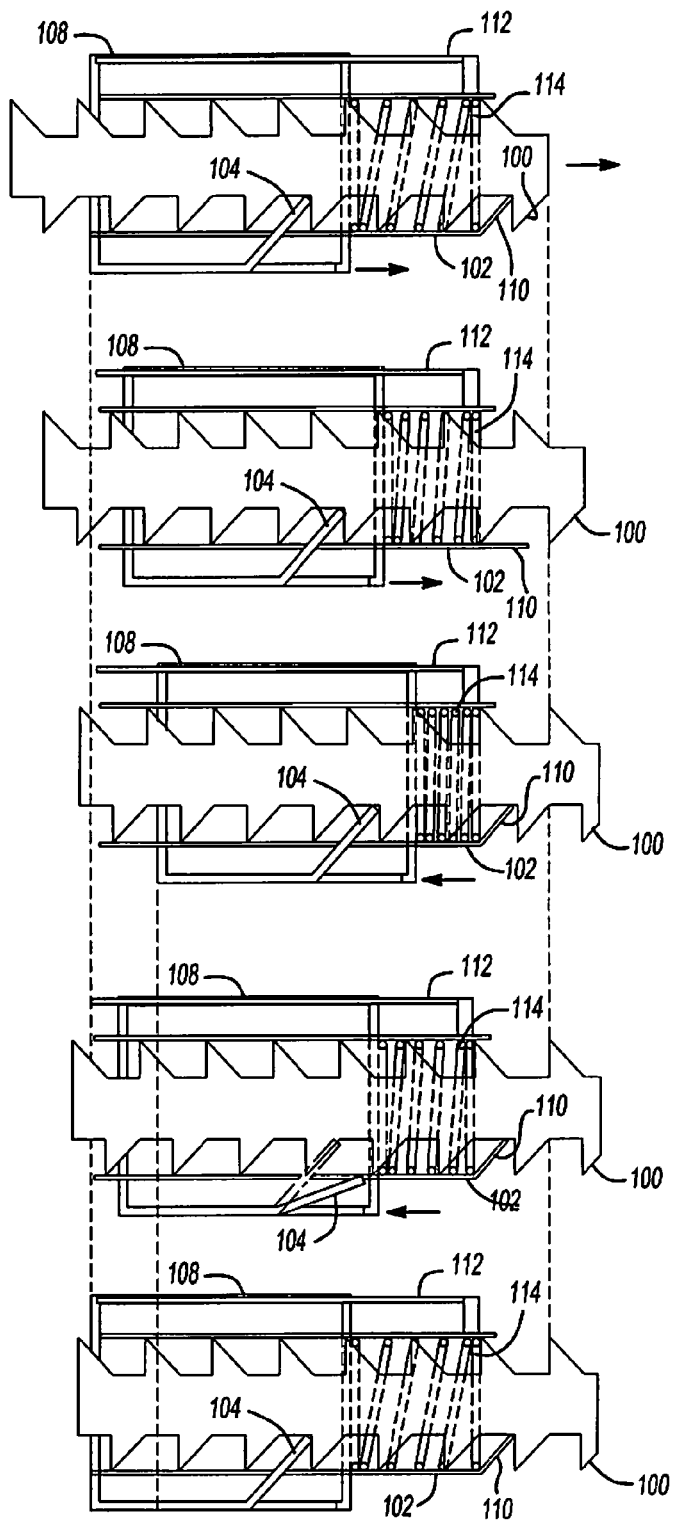

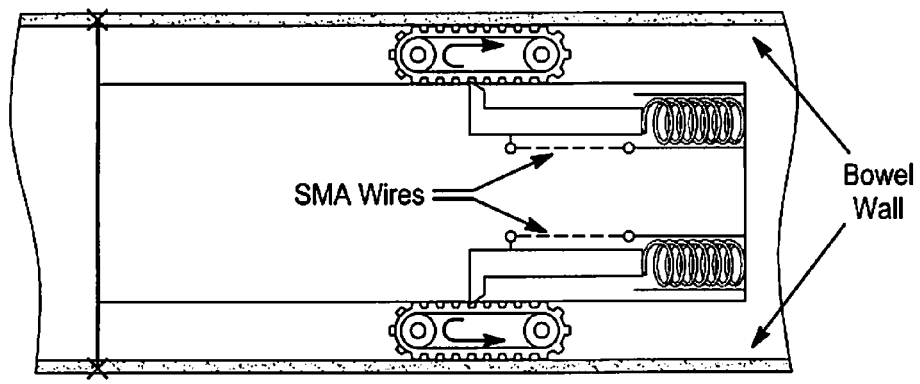
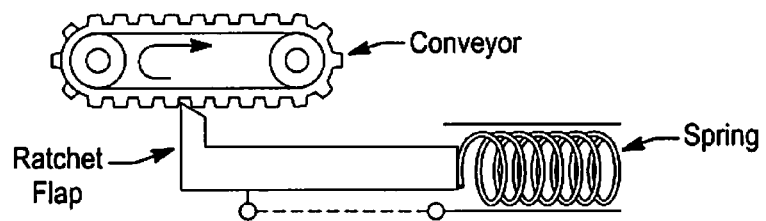
Fig-20
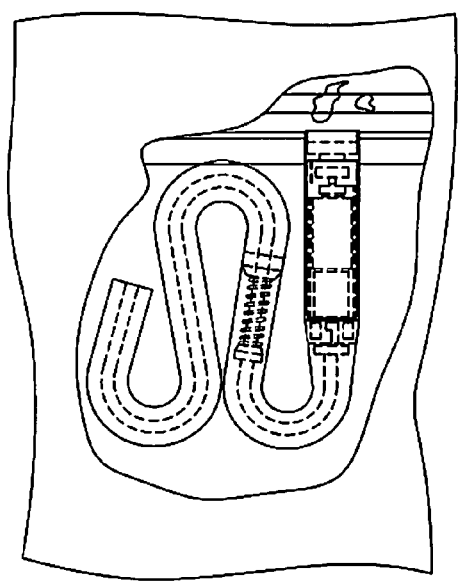
Fig-21

MECHANICAL EXTENSION IMPLANTS FOR SHORT BOWEL SYNDROME

CROSS-REFERENCE TO RELATED APPLICATIONS

This application is a continuation-in-part of U.S. patent application Ser. No. 11/673,193 filed on Feb. 9, 2007, now U.S. Pat. No. 7,722,560 B2. This application also claims the benefit of U.S. Provisional Application No. 61/043,549 filed on Apr. 9, 2008. The entire disclosures of each of the above applications are incorporated herein by reference.

GOVERNMENT INTEREST

This invention was made with government support under DK075413, awarded by the National Institutes of Health. The government has certain rights in the invention.

FIELD

The present disclosure relates to mechanical extension implants and, more particularly, mechanical extension implants for use in the linear extension of the gastrointestinal tract; including the esophagus, small intestine, and large intestine.

BACKGROUND AND SUMMARY

The statements in this section merely provide background information related to the present disclosure and may not constitute prior art.

Short-bowel syndrome (SBS) is a devastating disease associated with mortality rates exceeding 30%. It is a condition where the small intestinal length is far less than required for proper nutrient absorption. This condition can occur in pediatric and adult populations, and may be due to congenital processes, or acquired through the loss of large amounts of small intestine due to inflammatory conditions or ischemic events. The syndrome prevents a self-sustaining absorption of nutrients from the intestine, and supplemental parenteral nutrition is required. An estimated 40,000 patients with intestinal dysfunction from small bowel syndrome require parenteral nutrition. Several long-term effects due to parenteral nutrition have been found to be harmful, such as sepsis, liver disease, and bowel bacterial overgrowth; therefore, this method can only be used as a short-term solution. Care for small bowel syndrome patients is in excess of $200,000 per patient per year, and estimated costs in the United States have exceeded $1 billion yearly.

A number of treatment procedures have been proposed to alleviate small bowel syndrome. Some have tried using growth hormones along with specific nutrients known to stimulate bowel tissue growth. This approach has limited effectiveness and several obstacles, including reversal of the adaptive process after termination of the hormones, lack of somatic muscle growth, and concerns about uncontrolled and tumorous growth.

Another option is to surgically modify the organs to achieve an increase in intestinal length. With this approach, there is a risk of injury to the mesenteric vasculature, leakage of enteric contents due to a very long surgical connection, and the procedures can only be done if the intestine is overly dilated. Despite success in some patients, there is a very high failure rate up to 45% in some series.

Finally, small bowel transplantation has been used for adults and children when other treatments have failed. Although a viable option, transplantation is very costly. Patients require long-term immunosuppression and are at risk for infection and graft failure. Although early patient and graft survival are excellent, five-year graft survival is typically at the 50% level, and patient survival is approximately 60%. Clearly, there is a great need for an alternative procedure to treat short bowel syndrome.

Recently, the principles of the present teachings have demonstrated that mechanical forces can be powerful regulators of tissue growth or regeneration. Through the process of mechanotransduction—the translation of mechanical signals to biochemical ones which affect cell function—the response to the forces results in a cascade of actions which includes the activation of growth mechanisms. Numerous organs have been shown to be mechanoresponsive including bone, lung, and neural tissue. According to the principles of the present teachings, the controlled mechanical stimulation to the small intestine, such as through mechanotransduction of forces applied in a linear fashion to small bowel, can help induce intestinal growth.

According to the principles of the present teachings, implantable bowel extenders are provided that can be used to overcome the issues associated with small bowel syndrome. In some embodiments, the implantable bowel extender can be a hydraulic and/or a shape memory alloy (SMA) actuated device.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 2B is a schematic view illustrating the hydraulic bowel extender of FIG. 2A in an extended position;

FIG. 3 is a photograph of a hydraulic bowel extender according to the principles of the present teachings;

FIG. 4 is a perspective view illustrating a bowel extender according to the present teachings using a shape memory allow (SMA) drive system;

FIGS. 5A-5E is a series of partial cross-sectional views illustrating the SMA bowel extender of FIG. 4 through a drive cycle;

FIG. 20 illustrates an SMA ratchet driven conveyor, where the conveyor for continuous paying out can be actuated by a reciprocating SMA—spring pair acting through a ratchet mechanism on the belt;

FIG. 21 illustrates a track-follower device in body cavity, which is a CAD rendering of track-following bowel extender inside abdominal cavity taken from CT-scan data;

Figure 29:
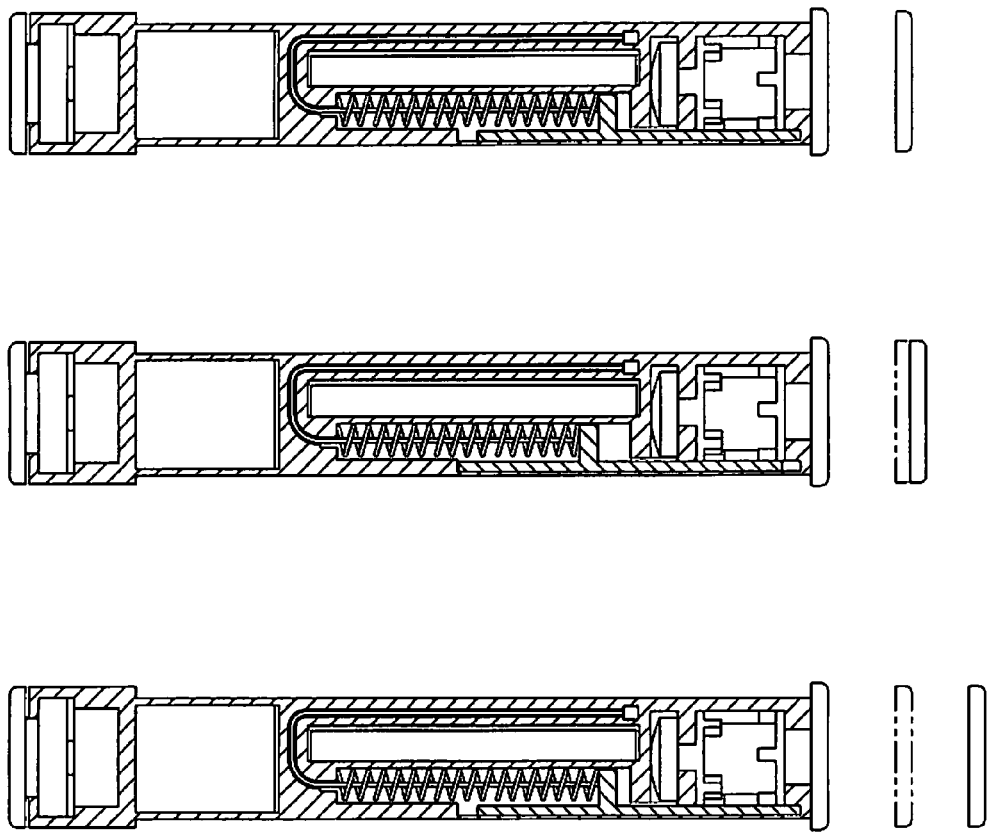
Figure 30:
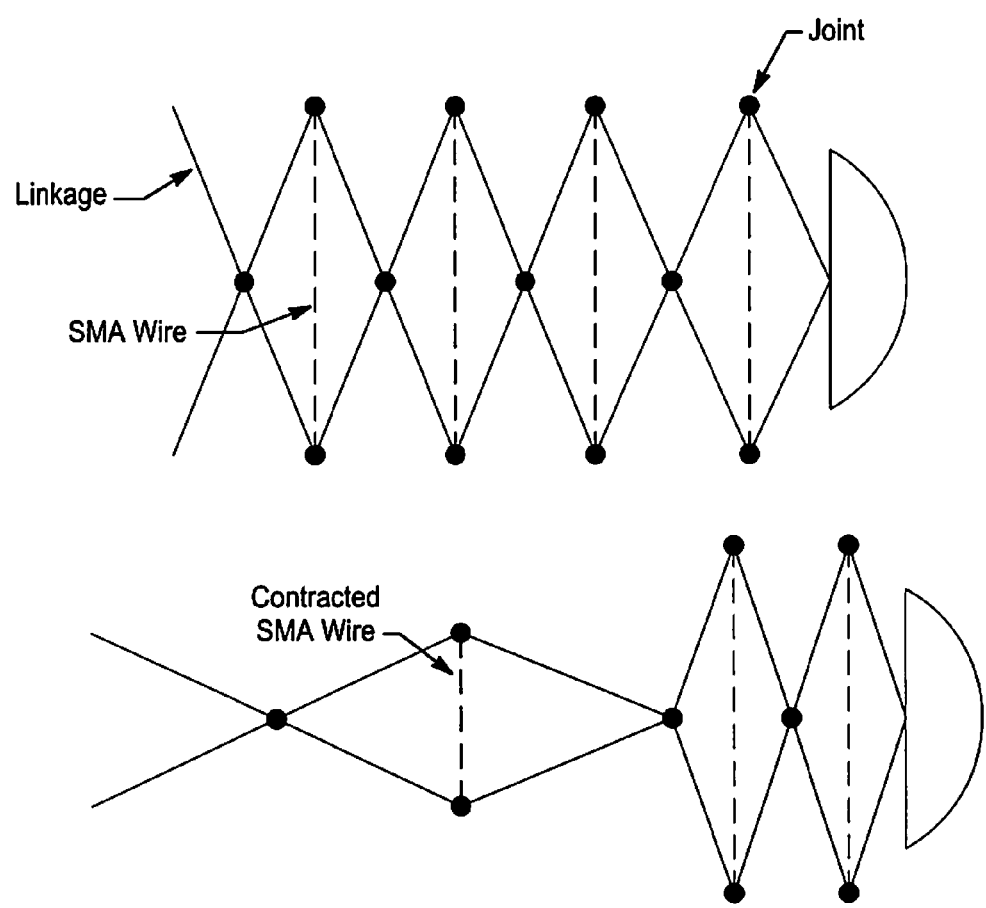

FIG. 29 illustrates the SMA escapement of the rotating-disc spring expander, where reciprocating motion of an SMA wire (red/blue)-spring (orange) pair moves a sliding element (blue) to incrementally engage alternately opposing teeth on a barrel-shaped escapement (yellow) which allows the coil spring (magenta) to incrementally unwind; and FIG. 30 illustrates a distributed SMA scissor mechanism, where a series of scissor mechanisms are individually actuated to cause incremental expansion of the whole device.

DETAILED DESCRIPTION

The following description is merely exemplary in nature and is not intended to limit the present disclosure, application, or uses.

Bowel extenders according to the principles of the present teachings, generally indicated at 10 in the accompanying figures, are designed to operate inside the human body cavity inserted in a section of bowel, which can remain intact in the digestive tract, or can be detached from the digestive tract yet remain attached to the vasculature. In cases where a section of bowel is detached, the remaining bowel can be reattached, thereby maintaining bowel function during the lengthening process. Bowel extender 10 extends gradually, and after treatment, the lengthened bowel segment can be anastomosed back into the digestive tract. It should be appreciated that the power, monitoring, and automatic control components can be integrated within the implanted device.

For clinical use, the implant design should meet a set of specifications based on the mechanical and growth properties of the bowel itself and the body cavity. To fit inside an average-sized adult human bowel, bowel extender 10 may have an outside diameter ranging from 1 cm to 2 cm, allowing enteric fluids and mucous to transit around the device. Bowel extender 10 should be relatively smooth, made of biocompatible materials, and should not generate external temperatures greater than 37° C. to avoid damaging the bowel tissue. The un-extended length of a bowel extender 10 which is placed in an isolated segment of bowel should range from 10 cm to 15 cm. For extenders which are placed into the normal continuity of the intestine, longer segments may be lengthened depending on the abdominal cavity dimensions of each patient. However, it should be appreciated that various sizes of bowel extender 10 may be manufactured for various sizes of patients. Ideally, the implant should extend to a minimum of twice its initial length, although further extension is always desirable and less extension may be acceptable in some cases.

Figure 1:
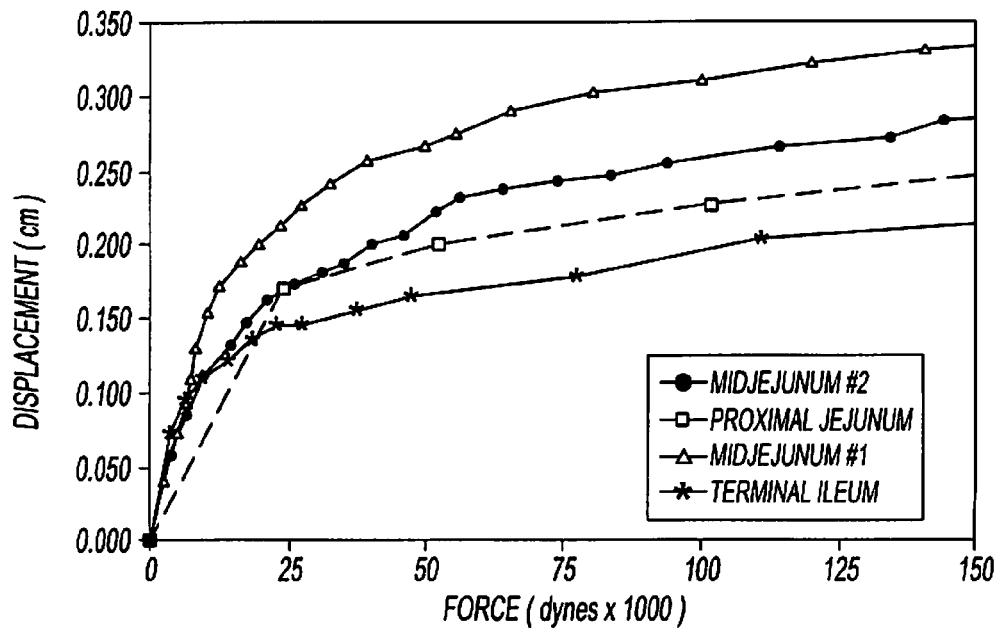
FIG. 1 is a graph illustrating force displacement characteristics of various portions of a small bowel where the dashed sloped indicates a safe range of force/displacement to avoid damage to the bowel.

To determine the forces required to stretch the bowel and the maximum force to avoid bowel damage, mechanical tests were conducted on sections of pig bowel similar in dimension to human bowel. A series of tensile loads were applied to a set of 10 cm bowel segments taken from various locations along the intestinal tract, and the relative change in length (strain) was measured. As illustrated in FIG. 1, the force-strain relationships plotted show a linear elastic region at loads below 10 gf (gram-force) above which the bowel becomes less stiff. Inspection of the bowel shows that no damage occurs at tensile loads below 35 gf and strains below 20%.

A key function of bowel extender 10 is to maintain the tensile force as the bowel grows, thus a static device is not sufficient because as the bowel grows it could lose contact with the device. Additionally, due to the slow growth rate of the bowel, the extension rate of bowel extender 10 does not need to be rapid and, thus, can be on the order of about 1 cm per day. This motion may be continuous, such as in connection with a hydraulic extender, or can define finite steps, such as in connection with an SMA actuated extender (each will be discussed in detail below).

For the finite step scenario, bowel extender 10 should hold the new length for a period of time after each step, such that the bowel can grow and "catch up" with bowel extender 10 before another step is taken. In some embodiments, these steps can occur when the patient is or known to be still. At other times, however, the patient may be moving, such that when holding a position, bowel extender 10 must hold against forces from the surrounding tissues larger than those occurring during a step, with a specified retention force set to 200 gf.

While the 35 gf safe limit allows a large, 2 cm step size, in practice, a smoother and slower lengthening is desired, with a 1 to 2 mm step size specification. A 2 mm step represents a 2% strain on a 10 cm bowel segment, with a corresponding tensile force of 1.4 gf. This, however, is simply the force required to stretch the bowel; additional force is required to push against the soft tissues surrounding the bowel. Therefore, the required extension force can be set to a range of 15 to 35 gf.

In some embodiments, bowel extender 10 can be used for extension only and thus need not be capable of retraction. However, it is anticipated that bowel extender 10 can be constructed to have a retraction function to aid in its removal.

Hydraulic Bowel Extender

Figure 2A:
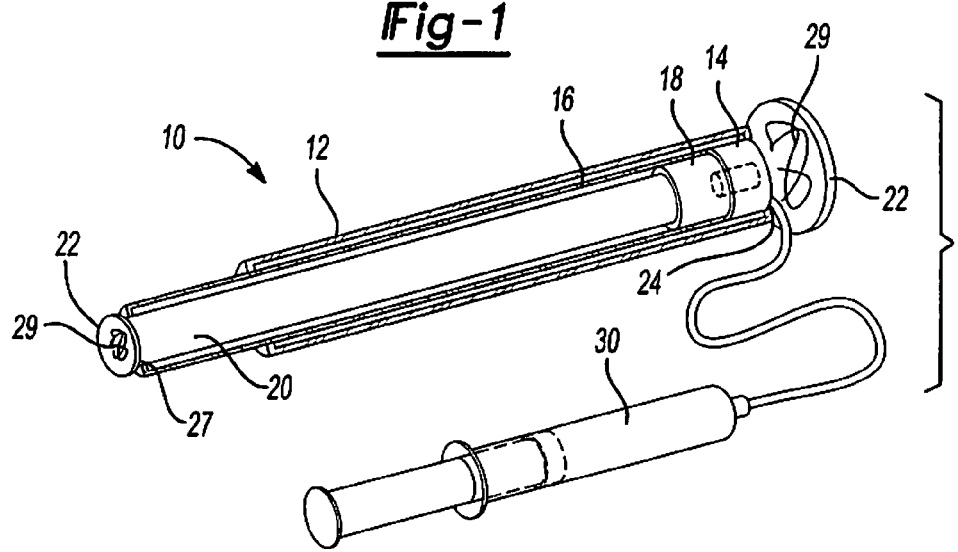
FIG. 2A is a schematic view illustrating a hydraulic bowel extender according to the present teachings in a retracted position.

In some embodiments of the present teachings, a clinically appropriate implantable bowel extension device is provided and generally referenced as a hydraulically-actuated bowel extender 10. Bowel extender 10 was used in connection with in-vivo lengthening experiments in pig small bowel as illustrated in FIGS. 2 and 3.

3.1. Device Architecture

Hydraulics provide a simple means of direct linear extension. In principle, a hydraulic piston can produce large motions with large forces as long as a high-pressure fluid source is available which can be difficult to implant, requiring connection through the skin to an external fluid source. The overall motion of a hydraulic piston is limited by the length of the cylinder, and is reduced by the additional length required for piston seals and hydraulic connection ports. To overcome the effects of this extra overhead and come near to the goal of a length-doubling extension, a dual concentric piston design was developed which provides approximately twice the motion of a single piston in a similar package size.

Bowel extender 10 (shown schematically in FIG. 2 and in the photograph in FIG. 3) comprises an outer syringe casing 12 (cut from a 3 ml, 10.2 mm diameter medical syringe) through which an outer syringe plunger 14 runs. The outer syringe plunger 14 is attached to and pushes forward an inner syringe 16 (cut from a 1 ml, 6.4 mm diameter medical syringe) through which another rubber plunger 18 runs. The inner syringe rubber plunger 18 pushes forward a push rod 20 which extends to the forward end of bowel extender 10. Silicone bumpers 22, which can be about 16 mm in diameter, on the back end 24 of outer syringe 12 and the front end 27 of push rod 20 apply extension forces against the ends of the bowel section. When saline fluid (chosen for biocompatibility) is forced into bowel extender 10 using a manually operated unmodified 10 ml syringe or actuation piston 30 as a pump, pressure from fluid in outer syringe 12 pushes forward the outer syringe plunger 14. A hole 15 through the outer syringe plunger 14 allows fluid to flow into inner syringe 16, pushing the inner syringe plunger 18 and push rod 20 forward. In some embodiments, the overall length of bowel extender 10, when retracted, is 11.8 cm. Outer piston system 26, including outer syringe 12, outer syringe plunger 14, and inner syringe 16, extends 5.7 cm beyond this length, and inner piston system 28, including inner syringe 16, plunger 18, and push rod 20, extends an additional 4.5 cm, for a total extended length of 22.0 cm: an 86% increase in length. It should be appreciated that bowel extender 10 can be configured with additional piston systems to achieve greater extension, such as 4-, 5-, or more fold.

3.2. Benchtop Characterization

Benchtop tests were performed to validate the basic operation of the dual hydraulic embodiment of bowel extender 10 and to determine both the forces on actuation piston 30 required to produce motion and the holding power of bowel extender 10. Because of the large diameter of actuation piston 30, relatively large forces are required to actuate bowel extender 10 to overcome friction in the pistons and to produce motion. To measure these forces, actuation piston 30 was mounted vertically in a vice and increasingly large weights placed on the actuation piston 30 until motion was produced in bowel extender 10. Since the diameter of outer piston system 26 was larger than the diameter of the inner piston system 28, the outer piston system 26 moved first, requiring a 2200 gf weight on actuation piston 30. Once actuation piston 30 reached its full extension, weight was gradually added until a total of 6900 gf of weight caused inner piston system 28 to move to its full extension. The 2200 gf weight corresponds to a fluid pressure of 103 kPa gage (15 psi), or a force of 640 gf on outer piston system 26 to overcome friction. Similarly, the 6900 gf of weight corresponds to a fluid pressure of 324 kPa gage (47 psi), or a force of 648 gf on inner piston system 28 to overcome friction. To measure the holding capacity of bowel extender 10, when actuation piston 30 is left free to move, bowel extender 10 was pushed against a digital scale until each piston retracted. Inner piston system 28 retracted first, with a force of 400 gf, twice the required 200 gf, after which outer piston system 26 retracted with a force of 900 gf.

3.3. In-Vivo Experiments

A population of eleven (11) young adult pigs was implanted with the dual hydraulic embodiment of bowel extender 10. In each pig, two 11 cm lengths of bowel were isolated from the digestive tract (suspended on its mesentery), and the remaining bowel reconnected. Both segments had a hydraulic extender inserted, and the ends were oversewn. The tubing which connected to actuation piston 30 was brought out through one end. One of the two segments acted as a control, and no fluid was pumped into bowel extender 10. The other underwent an incremental lengthening (0.5 ml, or approximately 1.46 cm per day) over the course of seven days, until bowel extender 10 was fully extended (10.2 cm). All but one pig had a successful trial: the first pig developed an intestinal leak due to a buildup of mucus, which was drained in the remaining 10 pigs, and this initial pig had to be sacrificed on the third day of extension.

After the extension procedure, the small bowel segment length, weight, and surface area were compared between the control segments and the extended segments in Table 1:

| Group | Length (cm) | Wet Weight (g) | Surface area (cm$^2$) | Mass/cm$^2$ |
|---|---|---|---|---|
| Control | 10.4 ± 3.2 | 17.4 ± 4.5 | 46.1 ± 13.7 | 0.33 ± 0.04 |
| Lengthened | 17.6 ± 2.4* | 29.4 ± 2.3* | 86.7 ± 19.8* | 0.28 ± 0.03 |

As can be seen from the table above, the lengthened segments were 69% longer, 69% heavier, and include 88% more surface area relative to the Control segments. Additionally, the mass per cm$^2$ decreased only slightly, by 15%, indicating that the lengthened bowel has potentially similar structure and function to normal intestine.

3.4 Preliminary Data On Implanted Devices

Histology: Mucosal thickness and crypt depth was much greater in the Lengthened group versus the Control group as illustrated in Table 2:

TABLE 2

| Group | Villus height (μm) | Crypt depth (μm) | Mucosal thickness (μm) |
|---|---|---|---|
| Control | 324 ± 76 | 365 ± 43 | 647 ± 75 |
| Lengthened | 353 ± 76 | 450 ± 95* | 772 ± 134 |
| Jejunum | 522 ± 87 | 341 ± 64 | 842 ± 75 |

Villus heights, however, were reduced in both the Lengthened and Control groups compared to the adjacent jejunal segment; most likely because both segments were taken out of continuity with normal enteric flow. In contrast, crypt depth dramatically increased in the Lengthened segment compared to both the Control and jejunal segments. Increased crypt depth was accompanied by an increase in epithelial proliferation. Epithelial cell (EC) proliferation (% of proliferating crypts) showed a significant (P<0.05) increase in crypt cell proliferation in the Lengthened (26.30±3.3) versus the Control (15.67±5.70) and adjacent jejunal (12.09±5.9) groups. Importantly, gross and histologic inspection did not show evidence of mechanical injury to the lengthened segments of bowel.

Physiologic changes after lengthening: DNA and RNA content did not differ between the Lengthened and Control groups. Using chamber studies were performed to assess the mucosal epithelial absorption and epithelial secretory function, as well as epithelial barrier function of the Lengthened segment. The Lengthened group, in this case was compared to normal jejunum, in order to determine the differences and/or similarities between normal functioning bowel and the elongated segment. Epithelial barrier function in Lengthened versus normal jejunum were measured by changes in transepithelial passage of [3H]-mannitol and transepithelial resistance (TER). Transepithelial passage of [3H]-mannitol remained unchanged. However, a decline in barrier function was observed when measured by transepithelial resistance (TER) as illustrated in Table 3:

TABLE 3

| Group | [3H]-mannitol | TER | Glucose-mediated sodium transport ($\mu A/cm^2$) | Carbachol-mediated chloride transport ($\mu A/cm^2$) |
|---|---|---|---|---|
| Jejunm | 0.16 ± 0.08 | 11.5 ± 0.9 | 18.1 ± 5.4 | 11.4 ± 2.9 |
| Lengthened | 0.17 ± 0.08 | 10.2 ± 0.4* | 8.8 ± 2.0** | 11.8 ± 2.9 |

Carbachol-induced epithelial chloride transport was not significantly different compared to normal jejunum (P=0.67). Glucose-mediated epithelial sodium transport, however, was decreased in the Lengthened group compared to normal jejunum.

Investigation into the mechanisms responsible for enterogenesis: Based on previous work with mechanotransduction models in various organ systems, a number of factors were identified that, at least in part, might be responsible for mediating the growth of the small bowel in these experiments. The mRNA expression of several factors derived from mucosal scrapings of Lengthened and Control segments of bowel is illustrated in Table 4:

TABLE 4

| Group | Occluden | Proglucagon | Alpha-E integrin | C-Src | Wnt5a | E-Cadherin | Hedgehog (Indian) |
|---|---|---|---|---|---|---|---|
| Control | 0.89 ± 0.09 | 0.42 ± 0.18 | 0.58 ± 0.07 | 0.28 ± 0.01 | 0.08 ± 0.02 | 0.27 ± 0.02 | 0.28 ± 0.07 |
| Lengthened | 0.98 ± 0.09 | 0.55 ± 0.22 | 0.58 ± 0.20 | 0.43 ± 0.10* | 0.16 ± 0.04* | 0.32 ± 0.04 | 0.29 ± 0.14 |

Of note was a significant (2-fold) increase in the expression of C-Src and Wnt in the Lengthened group. Wnt 5a was selected as a known inducer of intestinal embryogenesis 1, 2. E-Cadherin and proglucagon (precursor to GLP-2) increased, but changes were not significant. This suggests that both Integrin-mediated and Wnt signaling pathways which may help mediate distraction-induced enterogenesis in this pig model.

Protein Expression: Differential protein analysis of factors expressed in the Lengthened versus Control group was performed with 2-D gel electrophoresis (University Protein Core, N=3). A secondary mass spectrogram analysis was performed (Applied Biosystems, Foster City, Calif.) of 6 proteins which were only expressed in the Lengthened group. This included an expansion of desmin, vimentin and beta actin profilin complex. Other proteins which may or may not have relevance to enterogenesis include: alpha-1-antichymotrypsin, condensin subunit 1 and immunoglobulin lambda-chain. The finding of increased desmin and vimentin (expression>95% confidence interval) strongly supports a Wnt-mediated signaling pathway as these factors are exclusively expressed in the mucosa of developing intestine during increased Wnt expression.

While further study is required to determine the function of the lengthened bowel relative to normal intestine, the hydraulic extender 10 clearly demonstrates that an implantable extension device has the potential to become a useful clinical device for treatment of short bowel syndrome, and is worthy of further development and testing. However, the foregoing should not be interpreted as precluding the use of the hydraulic bowel extender 10, but rather simply enumerating that additional modification can be made to the present teachings without departing from the spirit of such teachings.

3.5. Reimplantation of Lengthened Bowel into the Normal Continuity of the Intestine Rationale: It has been shown herein that according to the principles of the present teachings, the length of an isolated intestinal segment can be doubled with the application of linearly directed distractive forces over a predetermined time period (such as 7 days), thus resulting in increased surface area and epithelial cell proliferation. In order to evaluate the function of these lengthened segments after re-implantation into normal jejunum, reimplantation of the lengthened segment was performed.

Methods: Bowel extender 10 was inserted into isolated jejunal segments in pigs, and fully expanded over 8 days. A control intestinal segment contained bowel extender 10, but was not lengthened. Lengthened segments, numbering five (5) in total, were then re-implanted into normal intestinal continuity. Pigs were sacrificed after another 28 days. Function was assessed by motility and absorptive capacity of the bowel. Data (mean±SD) were analyzed using ANOVA and t-test;*P<0.05.

Results: Lengthened segments were significantly longer than control segments and had a nearly 2-fold greater surface area. Bowel lengthening was maintained, going from 9.4±1.7 cm at re-implantation to 11.3±1.9 cm after 28 days. Motility was assessed by upper GI transient time and passage of activated charcoal. Motility was similar to non-operated pigs (Upper GI, 5.4±0.8 hours versus 6.3±0.6 hours; re-implanted versus non-operative, passage of activated charcoal, 17.6±1.7 hours versus 17.1±1.3 hours). Smooth muscle cells (2.5×104) were harvested from lengthened bowel and assessed for contractility 30 seconds after application of acetylcholine. A transient decline in function was seen after 8 days of lengthening (24.5±0.5 versus 51.6±1.0; % contraction from baseline in lengthened versus non-operated bowel); however contractility began to approach normal levels (38.3±0.9 versus 50.2±1.0) after re-implantation. Table 5 shows disaccharidase expression in the mucosa, and shows that these levels (which represent the absorptive capacity of the gastrointestinal tract) return to normal levels once the lengthened segment is replaced back into the normal continuity of the gastrointestinal tract.

TABLE 5

|  | Lactase | Sucrase | Isomaltase | Maltase |
| --- | --- | --- | --- | --- |
| Normal | 34.7 ± 13.7 | 36.3 ± 11.6 | 33.1 ± 13.0 | 120.2 ± 49.5 |
| Lengthened | 13.6 ± 4.8* | 21.8 ± 6.8 | 25.4 ± 13.2 | 106.6 ± 38.2 |
| Re-implanted | 30.8 ± 6.2 | 41.3 ± 18.5 | 42.1 ± 12.2 | 114.04 ± 4.5 |

Chamber experiments were done to further assess the absorptive capacity (Table 6). Similarly, although there are some losses of ion transport function immediately after the bowel is lengthened, these return to similar values to normal bowel once the lengthened segment is returned to the normal gastrointestinal continuity.

TABLE 6

|  | BF(%) | Baseline current ($\mu$A/cm2) | Ion-transport ($\mu$A/cm2) Na+ | Cl– |
| --- | --- | --- | --- | --- |
| Normal | 0.13 ± 0.04 | 11.0 ± 1.6 | 19.0 ± 4.0 | 16.9 ± 2.9 |
| Lengthened | 0.13 ± 0.04 | 8.9 ± 2.2# | 12.2 ± 2.2# | 11.4 ± 3.0# |
| Re-implanted | 0.13 ± 0.04 | 9.8 ± 3.8 | 18.4 ± 3.7 | 12.5 ± 3.7 |

Accordingly, it should be appreciated from the foregoing that bowel lengthening, according to the present teachings, results in a transient decline in mucosal absorptive function and smooth muscle contractility, while maintaining barrier function. However, function approaches that of normal bowel after re-implantation into enteric flow. Further, the gain in length is preserved after re-implantation.

4. SHAPE MEMORY ALLOY (SMA) BOWEL EXTENDER

Due to the compactness and implantability requirements of bowel extenders in many cases, conventional approaches are not viable due either to a) the external equipment necessary to drive them as in the case of hydraulics, or b) to their large size, such as in the case of electromechanical actuators. However, it should be appreciated that such arrangements are not to be regarded as being outside the scope of the present teachings and are intended to be part of the present disclosure. Shape memory alloy is an attractive alternative because it is unmatched on specific power (>100 kW/kg) and specific work (up to GJ/m3), and simultaneously produces high strains (3-8%) and high stresses (up to 50 GPa), which is necessary for very compact actuation systems as required in the bowel extender. SMA also operates at safe levels of voltage and current to activate via resistive heating, is relatively inexpensive, and extremely biocompatible and corrosion resistant. The main disadvantage of SMA is its inherent slowness, typically only a few hertz, resulting from the heating and cooling activation cycle. Fortunately, in this case, the desired response is slower than this and the heat can be mitigated via a thin layer of thermal insulation or by embedding the SMA material within the interior of bowel extender 10. The challenge in the design of SMA wire 112 based bowel extender is to transform the relatively small strains (3-8%) into a long, continuous motion (over many cm). To achieve this, a ratcheting approach based upon many cyclic steps was pursued.

4.1. Device Architecture

In general, shape memory alloys (SMA) undergo first-order diffusionless displacive transformations. When SMA's are heated they revert to their original Austenite form, regaining any strain imposed at lower temperatures when it is in its soft Martensite phase. An actuator (motor) can be formed by coupling the SMA with a spring that induces strain in the wire as it cools to its Martensite phase. Because the actuation strain in the SMA is limited to only a few percent, a linear ratcheting extension mechanism was conceived to accumulate these incremental motions to produce large displacements.

The basic design of SMA wire 112 bowel extender is a concentric tubular linear ratcheting mechanism, as illustrated in FIGS. 4-7, where a steel threaded push rod 100 slides inside a stainless steel outer shell 102, which has a ratchet flap 104 which engages in push rod 100 threads 106. A stainless steel movable collar 108 slides on outer shell 102 and also has a ratchet flap 110 which engages in push rod 100 threads 106. Ratchet flap 104 and ratchet flap 110 are designed such that they allow motion of push rod 100 in the extension direction only. An SMA (Nitinol) wire 112 is used as the actuator which, upon heating to the Austenite phase, can contract by 3-8% of its initial length. SMA wire 112 works against a return spring 114 which, when SMA wire 112 cools, stretches SMA wire 112 back to its initial length.

The resulting cyclic linear motion is used to actuate the ratchet system of ratchet flap 104 and ratchet flap 110, as shown in FIGS. 4-7. During the forward motion, the Austenitic SMA wire 112 (a) pulls the movable collar 108 forward (b) relative to outer shell 102, and pushes push rod 100 along with it due to collar ratchet flap 104 engagement (c), while the shell ratchet flap 110 disengages (d), allowing push rod 100 to slide forward (e). This motion compresses return spring 114 (f). When fully actuated, both movable collar 108 and push rod 100 have moved forward a distance Δ, return spring 114 is fully compressed (g), and the shell ratchet flap 110 reengages (h). As SMA wire 112 cools (i), return spring 114 stretches it back out, pushing the movable collar 108 back relative to outer shell 102 (j). During this motion, the shell ratchet flap 110 (k) holds push rod 100 in place (l) while collar ratchet flap 104 disengages (m), allowing movable collar 108 to slide back to its original position, after which movable collar 108 flap reengages (n) and return spring 114 is extended back to its original length. The net effect of this motion is to incrementally move push rod 100 forward by one or more thread teeth relative to outer shell 102. The front end of push rod 100 and the rear end of outer shell 102 thus push against the ends of the bowel segment, extending it.

4.2. Device Design

In the design of bowel extender 10, it is helpful to balance SMA wire 112 and return spring 114. During actuation, SMA wire 112 must be strong enough to compress return spring 114, overcome friction in the mechanism, and apply the specified 20 gf bowel load. During reset, return spring 114 must be designed to be just strong enough to stretch SMA wire 112 and overcome friction in the mechanism. While the friction force varies as the tooth engages and disengages with the ratchet, a maximum 379 gf load was measured and can be used as a conservative value for design purposes. An 8 mil diameter SMA wire 112 was chosen since it was experimentally determined to be capable of producing over 1600 gf of force. The 90 mm length of this wire was selected to be as long as can be reasonably mounted in bowel extender 10.

SMA wire 112 material lines were measured by gradually applying a tensile load and measuring deflection of both a cool (Martensitic) wire and an electrically heated (Austenitic) wire. A stock 53.6 gf/mm compression spring was selected with 9.14 mm diameter and 28.6 mm uncompressed length capable of producing forces up to 800 gf. The preload on return spring 114 was selected to stretch the wire to a maximum of 4% strain (requiring 137 gf), for a total force of 546 gf including friction and bowel load. After a 15% safety factor in reset was added, a 17 mm compressed length was used.

4.3. Prototype

A prototype was developed to test the principles of the present teachings. To this end, movable collar 108 and outer shell 102 were constructed from 0.25 mm wall thickness stainless steel tubing with flaps and tabs cut in. Push rod 100 was cut from standard 6.35 mm (0.25 in) diameter 1.27 mm (0.05 in) thread pitch (and equivalently single step size) stainless steel threaded rod. SMA wire 112 was attached at the leading edge of outer shell 102 and at the trailing end of movable collar 108. At the leading edge of movable collar 108, a flap was bent up to which SMA wire 112 was soldered using Nitinol Flux 400™ from Shape Memory Applications Inc., electrically connecting it to the bulk of bowel extender 10. Since the two ends of SMA wire 112 must be electrically isolated, the trailing end of movable collar 108 SMA wire 112 slips through a small slot in an additional Teflon collar and attaches to a rectangular brass crimp at the end of the slot, providing interference. This Teflon collar is the largest diameter feature on bowel extender 10 with an outer diameter of 10 mm. Electrical connection wires were soldered to the solder joint at the leading edge and to the brass crimp at the trailing end. Lumps of epoxy were attached to the front end of push rod 100 and the back end of outer shell 102 to provide smooth pushing surfaces.

The retracted length of bowel extender 10, and consequently both push rod 100 and outer shell 102, is about 10 cm. However, it should be appreciated that other lengths and sizes can be used depending upon the size of the patient or animal. While ideally, the full extended length of bowel extender 10 would be equal to the length of push rod 100 plus the length of outer shell 102 (a total of 20 cm), push rod 100 must remain engaged with both ratchet flap 104 and ratchet flap 110, noting that movable collar 108 flap lies behind return spring 114. Also, to maintain structural rigidity, push rod 100 must be partially retracted into outer shell 102. Thus, a certain degree of overhead is required and a full doubling in length is not possible. In this case, an 18 mm overhead length was required, allowing bowel extender 10 to extend to at maximum length of 18.2 cm, or 82% longer than its initial length.

4.4. Experimental Setup

To validate the design and performance of bowel extender 10, the prototype was tested to evaluate its ability to produce step motion under load. A test stand was used that allows the application of specified compressive loads to the end of bowel extender 10 during actuation and subsequent measurement during motion. The prototype device rests horizontally on a nylon bearing cylinder with the trailing end butted against an aluminum bracket. A variable weight hanging over the edge of the bench applies a compressive load to bowel extender 10 via a wire routed over a pulley and looped over the leading end of push rod 100. A non-contact MICROTRAK 7000 laser displacement sensor measures the deflection of the end of push rod 100. The data from the displacement transducer is recorded by a PC running Labview by means of an MIO-16E I/O board. Current is applied to SMA wire 112 from a KEPCO programmable DC power supply. The power supply was programmed to apply a square pulse in current of specified amplitude and time, and both the power input and bowel extender 10 motion were measured. The 0.8 A current used was determined empirically as the smallest current over which no addition motion occurs, fully transitioning the wire. Sequential steps were applied by cycling the current on for 10 seconds and then off for 20 seconds, giving plenty of time for SMA wire 112 to both heat and cool. Two sets of experiments were run to validate the operation and performance of bowel extender 10. First, external loads similar to those seen in stretching the bowel (0 to 50 gf) were applied and the stepping performance evaluated. Second, the ability of bowel extender 10 to step under larger loads (0 to 400 gf) was evaluated to determine the overall characteristics of bowel extender 10.

4.5. Benchtop Results

When actuated, bowel extender 10 pushes forward until SMA wire 112 is fully heated. This position may be somewhat ahead of a ratchet tooth such that when cooled, bowel extender 10 relaxes back to the previous tooth. At the end of 10 seconds of heating, under loads in the range of 0 to 50 gf (in steps of 10 gf), bowel extender 10 moved forward to a position which is independent of the load, varying by at most 2.8% around an average value of 2.52 mm. This position may be just past a ratchet step such that at the end of 20 seconds of cooling, bowel extender 10 can relax back to an average position of 2.47 mm (with a variance of 4.6% over load). In both the heated and cooled cases, there is no significant trend over load: noise and randomness in friction outweighed the loading effects. After a second, and further repeated heating/cooling cycles, bowel extender 10 displayed similar performance. The heated step motion was 10.5% larger than the predicted 2.28 mm heated step size. This difference can be attributed to the conservativeness of the prediction. Given that the 2.52 mm heated step size is equal to twice the 1.27 mm tooth spacing (within measurement error), bowel extender 10 took two ratchet steps rather than one, where each thread is 1.27 mm. This double-stepping would not cause a problem in the application because it is repeatable and because the double step size generates an elastic bowel force well below the 20 gf safety limit. Thus, it is demonstrated that bowel extender 10 has both the force and motion authority for the bowel application.

Under larger loads, ranging from 0 to 400 gf in steps of 50 gf, the motion was strongly dependent on the load and fell into three categories: double steps, single steps, and no steps. From 0 to 150 gf, performance was similar to that in the application load range, and bowel extender 10 moved just past the second tooth and took a double step. As the load was increased from 0 to 150 gf, the actuated motion was largely independent of the load, decreasing by only 7.5% (from 2.53 mm to 2.34 mm). This relative non-dependence on load is likely due to the fact that the ratchet tends to snap forward into place when approaching the next tooth (a behavior not predicted by the conservative model) bringing the mechanism farther forward than SMA wire 112 could do alone. From 200 to 350 gf, bowel extender 10 moved past the first tooth, by an amount dependent on the load, and relaxed back to a single step. Since the actuated motion in this range does not bring the ratchet near to a tooth (except at the high load end), the load dependence of the motion is much larger, decreasing by 43% (from 1.94 mm to 1.36 mm) as the load was increased. This test result validates that bowel extender 10 can reliably take steps against loads much higher (by a factor of 17.5) than the designed load of 20 gf. From 400 to 500 gf, bowel extender 10 could not generate much motion at all and took no steps, moving at most 0.16 mm when heated. While SMA wire 112 should have been able to generate motion in this range, the load was too high for the ratchet mechanism which slipped, not allowing movable collar 108 to push push rod 100 forward. Thus, the holding power of the ratchet was the force limitation, not SMA wire 112.

4.6. Ex-Vivo Experiments

To further validate the capabilities of the implant prototype and to provide insights into the performance, additional tests were run with bowel extender 10 inside an actual bowel section. A section of bowel slightly longer than the 10 cm retracted length of bowel extender 10 was removed from a pig. The entire device was enclosed in a loose latex bag to protect it from fluids and to both electrically and thermally insulate SMA wire 112. Bowel extender 10 was placed inside the bowel section and the ends of the bowel section tied closed to fit snugly against the ends of bowel extender 10. The open end of the latex bag extended through the tied end of the bowel, the tie keeping both the bowel and the bag closed, through which the electrical connection wires ran. Bowel extender 10 was actuated using the KEPCO power supply, applying a step sequence of 0.8 A for 10 seconds with 15 seconds between steps.

The test indicated that the implant successfully elongated inside the bowel section, acutely stretching the bowel. These tests demonstrate that SMA bowel extender 10 fits into and operates in the actual intraluminal environment of the intestine. Were the bowel allowed to grow as bowel extender 10 extended over a longer period of time, the forces would have remained well within the capabilities of bowel extender 10, allowing bowel extender 10 to extend to its full 82% capacity.

4.7. Advantages and Technical Challenges of SMAs:

The foregoing indicates that the SMA device embodiment of bowel extender 10 overcomes some of the shortcomings of the hydraulic expander embodiment of bowel extender 10. As such, bowel extender 10 is of an implantable size, and it is anticipated that, the power supply and controller could similarly be implanted (in the manner of a pacemaker), with a telemetery unit designed to control the unit. Since the steps are small, discrete, and reliable, the motion that is generated is easily predictable and controlled. A failsafe exists in bowel extender 10 in that even if the actuation current is maintained for a long period of time, bowel extender 10 will only take one step, and thus the bowel tissue cannot be overextended without purposely cycling the current to take many steps in sequence. In addition, the stepping is consistent and the ratchet mechanism rigidly holds its length after each step.

5. ADDITIONAL EMBODIMENTS

Increased Expansion Of Bowel Extender 10: As discussed herein, SMA bowel extender 10 achieves an expansion of 82% over the initial length of bowel. To produce a greater range of experimental data, in particular in connection with a clinical device, a modified version of bowel extender 10 (see FIG. 6 comprises two concentric linear ratchet mechanisms actuated by SMA wire 112, but moving in opposite directions. Thus, a greater than 2.5-fold expansion of the bowel will be achieved, allowing for better assessment of the lengthening capacity of the bowel.

Figure 6:
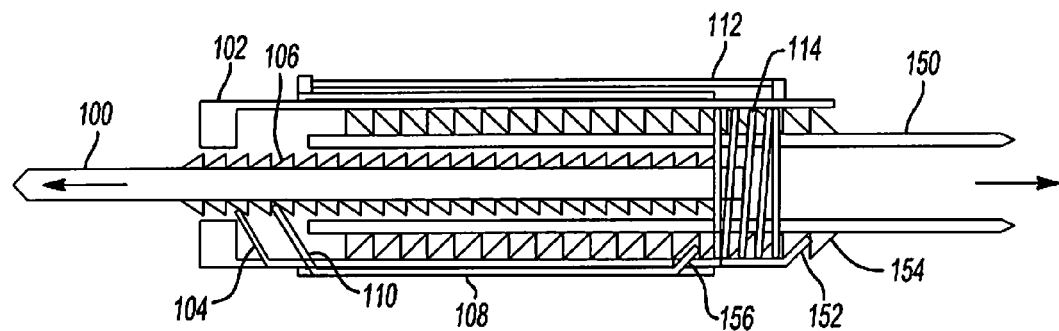
FIG. 6 is a cross-sectional view illustrating a bowel extender according to the present teachings using an SMA drive system to extend in opposing directions.

With particular reference to FIG. 6, bowel extender 10 comprises a hollow inner threaded rod 150 inside which a smaller threaded rod 100 is placed. A second, reverse-oriented flap 152 is installed in outer shell 102 which engages in threads 154 of hollow threaded rod 150. A reverse-oriented flap 156 on movable collar 108 engages the threads 154 of the hollow threaded rod 150. Upon activation of the SMA, the movable collar 108 will pull forward relative to outer shell 102, which will push the hollow threaded rod 150 forward while the inner rod 100 is held in place by the ratchet flap from outer shell 102. When the SMA relaxes, return spring 114 pushes movable collar 108 back, pushing the inner threaded rod backwards with it while the hollow threaded rod is held in place by the ratchet flap from outer shell 102. In this way, after one cycle, the outer threaded rod 150 moves forward a step, and the inner threaded rod 100 moves backward a step, expanding bowel extender 10 from both ends. Supports for the inner threaded rod 100 will be mounted inside outer shell 102 to maintain rigidity as the inner rod 100 comes out of the hollow rod 150. Since bowel extender 10 expands out both ends from its initial length, it can expand to a theoretical maximum of three times its initial length. The actual expansion (2.5-fold) will be less due to the lengths required for the flaps and for overall rigidity.

Concept For Improving The Safety Monitoring And Control Of Bowel Extender 10: To measure the tensile force bowel extender 10 is applying to the bowel section, load cells may be placed on one or both ends of bowel extender 10. While only one end is required to measure the applied force, the second end can be instrumented for redundancy, and to detect the presence of uneven traction forces along the bowel section. Subminiature, very low profile force transducers are available, from OMEGA (Stamford, Conn.) for example, with less than 10 mm diameter and 3 mm thickness which can be mounted between the end of each threaded rod and its rounded siliconized bumper. Such devices have a 1.3 mm wire to carry the force signal, which can be passed out along with the SMA power wires. The extension length of bowel extender 10 may also be measured by radiopaque markers 29 (FIGS. 2A and 2B) at each end. The transducer output will be recorded via a National Instruments NI DAQ 6052-E data acquisition card in a personal computer through Labview.

Monitoring The Expansion Of Bowel Extender 10: To monitor the expansion of bowel extender 10, and to ensure that bowel extender 10 actually does take a step, a hall-effect sensor/permanent magnet pair can be mounted between two moving sections. In some embodiments, the hall effect sensor can be mounted on the movable collar 108, and the permanent magnet mounted on outer shell 102. Small, low profile hall effect sensors with dimensions 4 mm×1.5 mm×3 mm are commonly available, for example from ALLEGRO MICROSYSTEMS INC. which can output a voltage in proportion to the strength of a magnetic field. The distance to a small, rare-earth magnet can be thus measured, and the incremental motion of the ratcheting device detected. In this way, the motion at each step can be monitored and both failed and double steps can be detected. By counting successful steps, the overall extension motion can be recorded.

Lengthening Device With Implantation Into The Normal Enteric Flow, Without Creation Of A Separate Limb Of Bowel: Although creation of a separate limb of bowel is acceptable, it could result in the loss of intestine because of the surgical manipulation of the bowel and resection of the operated portions at both ends, thus not maximizing the lengthened segment of bowel created. Further, a second surgery on the intestine may be associated with severe adhesions and risks injury to the intestine, itself. To address this, a more improved concept of a totally implanted device which is placed within the continuity of the intestine has been devised.

Figure 7:
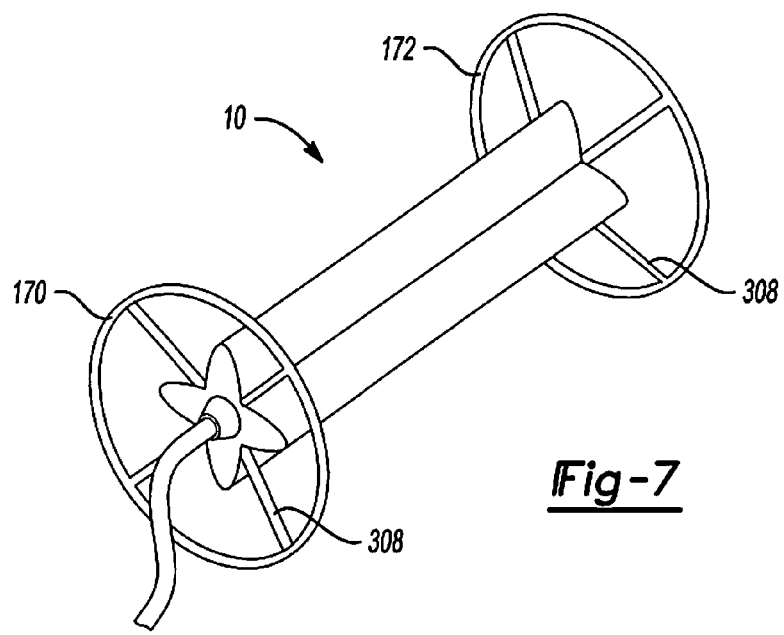
FIG. 7 is a perspective view illustrating a bowel extender according to the present teachings being implantable within a bowel without the need to remove a segment of the bowel from the digestive tract.
Figures 8A, 8B, 8C:
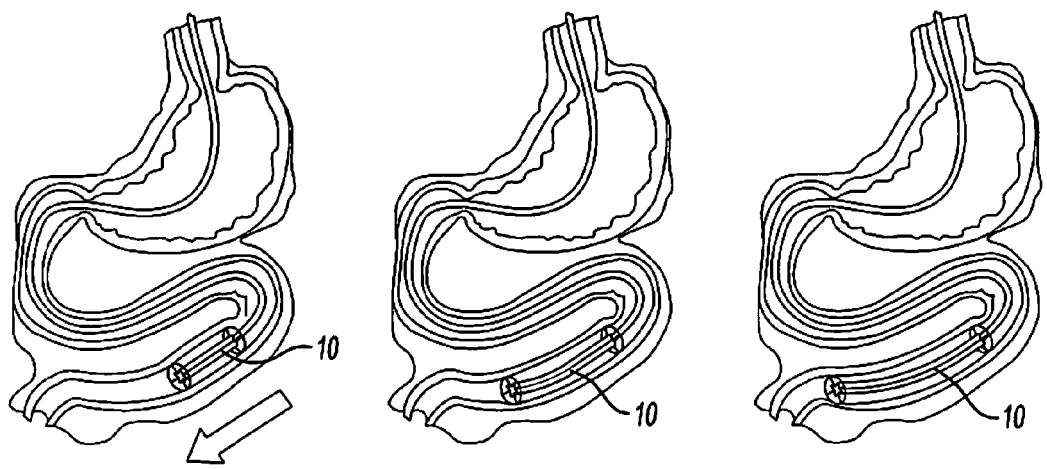
FIGS. 8A-8C is a series of cross-sectional views illustrating placement of the bowel extender of FIG. 7 within a body and the progressive steps of such bowel lengthening process.

With particular reference to FIGS. 7 and 8, it can be seen that bowel extender 10 can be suspended within the lumen of the bowel. Fixation points 170 and 172 at both ends of bowel extender 10 will consist of a biocompatible material (such as polytetrafluoride (GORTEX)), but also a material of non-viable connective tissue (such as SURGISIS). Fixation points 170 and 172 can be a ring of material which is sewn to the intestinal lumen with either absorbable or non-absorbable suture. This fixation ring will be attached to the bowel extender at multiple points to equalize the creation of distractive forces circumferentially. The diameter of bowel extender 10, in some embodiments, can be sized such that it is small enough that it will allow for enteric contents to move around and/or between bowel extender 10 and the fixation rings 170, 172, thus, preventing an obstruction of the bowel.

With particular reference to FIGS. 10-15, bowel extender 10 can comprise an outer syringe casing 300 being generally elongated having a rounded end portion 302. Rounded end portion 302 can comprise a hydraulic well 304 for receiving hydraulic fluid and a plurality of holes 306 for receiving ties 308 (FIGS. 7 and 8) supporting fixation points 170, 172. Outer syringe casing 300 further comprises a plurality of stop members 310 extending inwardly within an internal volume of outer syringe casing 300. The plurality of stop members 310 are sized to engage a corresponding plurality of gaps formed in inner members to prevent further extension thereof, as will be described.

Bowel extender 10 can further comprise an inner syringe casing 320 being generally elongated having a rounded end portion 322. Rounded end portion 322 can comprise a hydraulic well 324 for receiving hydraulic fluid. Inner syringe casing 320 further comprises a plurality of stop members 330 extending inwardly within an internal volume of inner syringe casing 320. Inner syringe casing 320 still further comprises a plurality of gaps or depressions 332 formed in an exterior surface of inner syringe casing 320. The plurality of gaps 332 are arranged and sized to engage with the plurality of stop members 310 to prevent further extension thereof. The plurality of stop members 310 and plurality of gaps 332 can further comprise a complimentary sloped surface 334 to permit simple collapse of bowel extender 10 when needed.

Inner syringe casing 320 can further comprise a seal member 336, such as O-rings, to aid in the fluidic sealing of inner syringe casing 320 relative to outer syringe casing 300. Additional casings can be used having similar construction as disclosed.

Control of the distracting forces (either hydraulic or electrical) as well as the monitoring of tension and length of the expansion will be carried out through tube which will extend from bowel extender 10 itself (in the case of esophageal or small bowel lengthening) through the nares. In this setting, the patient would have a naso-enteric tube throughout the duration of the lengthening procedure. In the case of a lengthening of the large bowel, this catheter would either exit through the entire large and small bowel and out the nose, or exit via the stomach or through the bowel and abdominal wall.

Figure 9:
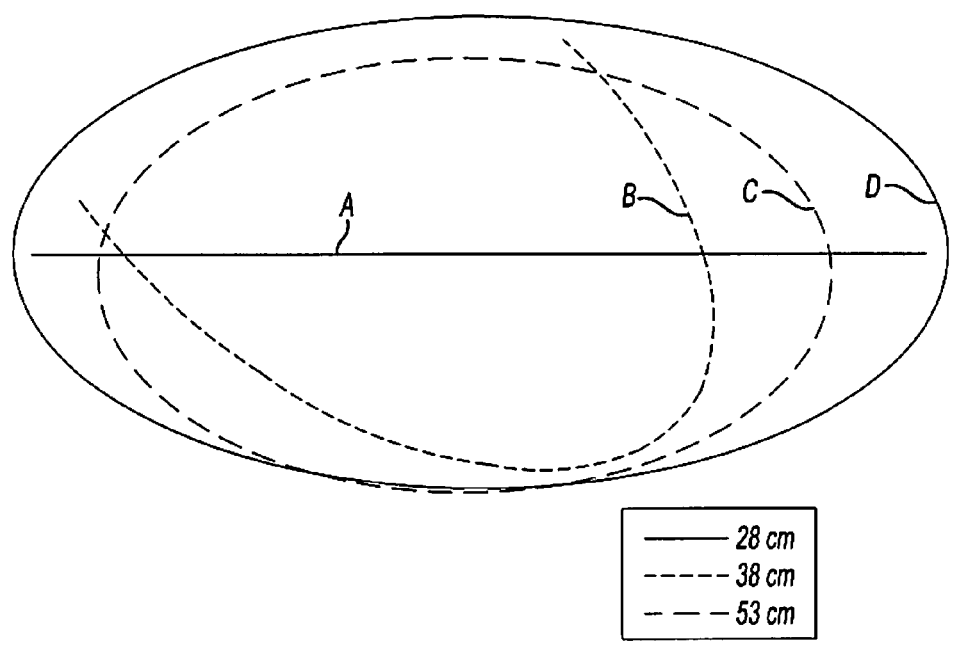
FIG. 9 is a schematic view illustrating various extension configurations when disposed in a body cavity.
Figure 10:
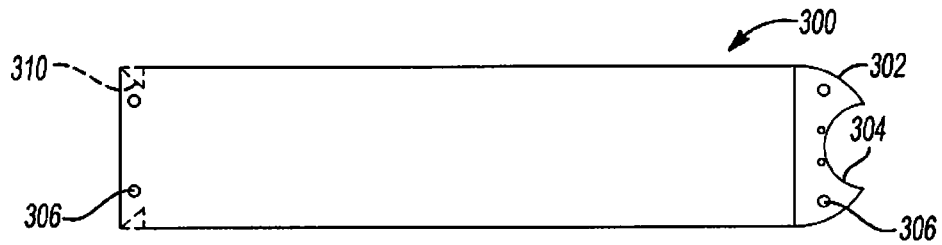
FIG. 10 is a side view, with portion hidden, of an outer syringe casing according to the present teachings.
Figure 11:
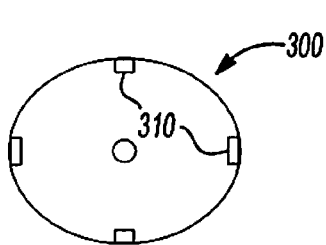
FIG. 11 is a rear view of the outer syringe casing according to the present teachings.
Figure 12:
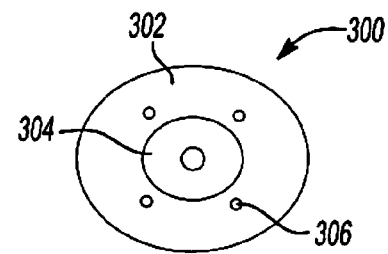
FIG. 12 is a front view of the outer syringe casing according to the present teachings.
Figure 13:
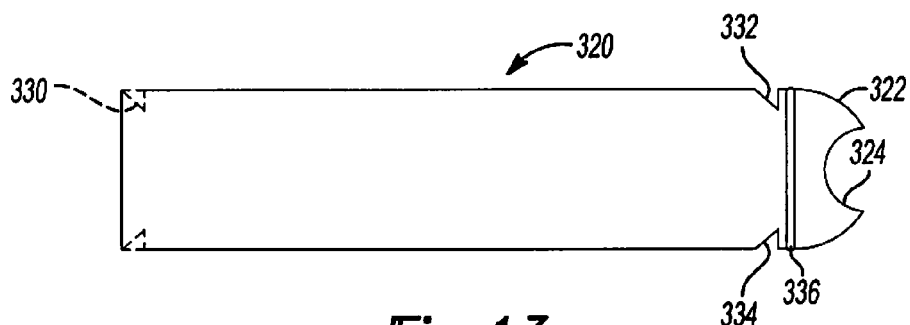
FIG. 13 is a side view, with portion hidden, of an inner syringe casing according to the present teachings.
Figure 14:
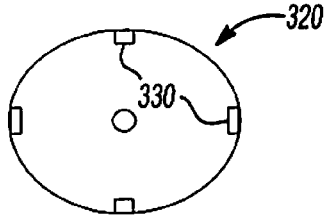
FIG. 14 is a rear view of the inner syringe casing according to the present teachings.
Figure 15:
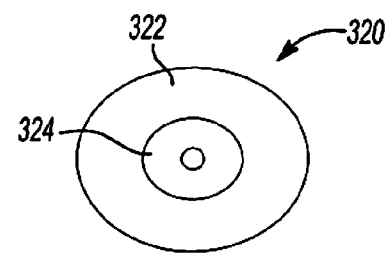
FIG. 15 is a front view of the inner syringe casing according to the present teachings.

In order to proceed beyond a 2.5-fold expansion, bowel expander 10 can be curved in shape to fit within the abdominal cavity as it expands beyond the longest dimension of the cavity as illustrated in FIG. 9. Two possible methods to achieve this include 1) constructing either the hydraulic, SMA ratcheting, or otherwise actuated expanders with a circular arc shape to each segment which form a longer arc length of the same curvature when expanded, and/or 2) constructing either the hydraulic, SMA ratcheting, or otherwise actuated expander with flexible elements which expanding linearly but can conform to the curvature of the abdominal cavity. As can be seen in FIG. 9, bowel extender 10 can be straight (Line A), can curve a small portion (Line B) or can curve a greater portion (Line C), yet be maintained within the patient's body cavity (Line D).

Upon achieving full extension and lengthening, bowel extender 10 can be retrieved with a flexible endoscope which can be introduced via the mouth or anal canal, and the sutures fixing the fixation rings to the bowel wall can be cut, device retracted, and device removed either via the mouth or anal canal.

6. CONCLUSION

Two devices developed as proof of concept for an implantable solution to bowel extension for the treatment of small bowel syndrome have been successfully demonstrated. Using a simple hydraulic device, promising results in a study using pigs has validated the viability of the use of mechanotransduction as a means to induce bowel growth. A shape memory alloy based ratcheting device has demonstrated the possibility of a fully implantable motion-controllable device.

ADDITIONAL EMBODIMENTS AND DISCUSSION

A description of the occurrence, causes, and effects of Short Bowel Syndrome (SBS) along with a description of the methods, high costs, and relatively low effectiveness of existing treatments is discussed above. The discussion herein describes a relatively unexplored mode of treatment using mechanotransduction where tensile forces on the bowel are employed to induce growth. A brief summary of the state of the art of mechanostransductive treatment devices follows:

The first class of existing devices referred to herein as externally mounted devices employs trans-body wall extension devices based on a linear screw which is mounted outside the body through a hole in the abdominal wall and into the and exposed segment of bowel which is removed from continuity of the digestive tract. A screw is manually advanced over time which applies tension to the bowel inducing growth. This class of device has been demonstrated successfully in rabbits and rats.

The second class of existing devices referred to herein as segment-implanted lengthening devices are implanted within a segment of bowel which is removed from continuity of the digestive tract. The device occupies (either inside or outside) the entire segment, and is actuated to lengthen over time, thereby applying distractive forces to the bowel segment and inducing growth. Such a device may or may not be entirely contained within the lumen of the bowel, may or may not be entirely contained within the body, and may or may not be explicitly attached to the bowel itself (where a device mounted inside the segment with the ends of the segment sutured closed simply pushes against the ends from the inside as it lengthens). After lengthening, the device is removed and the lengthened segment of bowel is re-inserted into continuity of the digestive tract.

The third class of existing device referred to herein as in-continuity implanted lengthening devices are implanted within the bowel without requiring the bowel segment to be removed from continuity. In this case, the device must not block the bowel, so fluids within the bowel must be able to flow around or through the device. The device is attached to the bowel at each end and the device is actuated to lengthen over time, thereby applying distractive forces to the bowel segment and inducing growth. Such a device may or may not be entirely contained within the body, and may or may not reside inside the lumen of the bowel (it can attach from the inside or the outside). After lengthening, the device is detached from the bowel at both ends and removed.

The second and third classes of existing devices have been discussed above, namely a linear telescoping hydraulic device, and a linear ratcheting device employing Shape Memory Alloy (SMA) actuation. Several issues have been discussed in the background material of the present application along with some concepts presented for enhancing the embodiments to address these issues. In particular, the following issues were discussed:

Manifold expansion: since both classes of devices discussed above can induce growth only up to the extent to which the device itself can expand, to obtain large amounts of growth, the device itself must expand several times its original length (preferably 3 to 5 times). The above embodiments addresses this by adding a series of telescoping actuation stages to each embodiment which, while increasing the complexity of the device, can multiply the expansion capabilities.

Curvilinear expansion: to obtain large amounts of growth from an initial segment, the classes of devices must themselves conform to the shape of the body cavity as the device lengthens. This was addressed above by either shaping the devices in a circular arc, pre-shaped to conform to the body cavity, or by constructing the devices to be flexible to conform to the body cavity. In both cases, the expansion capabilities of the device are enhanced but are still somewhat limited by the body cavity shape.

Monitoring and Control: the above techniques cover general concepts and some specific embodiments for adding sensing and monitoring capabilities with specific embodiments for including a load cell and for measuring incremental motion using a hall-effect sensor/magnet pair.

However, the following addresses new and different approaches for devices for treating short bowel syndrome with novel methods in several categories of functionality: bowel attachment, expansion class, and motion generation.

New Bowel Attachment Techniques

Two attachment approaches are discussed above: an end-abutting approach, where the bowel segment is closed off on the end and the device pushes against the closed end from the inside, and a sewn-in approach, where a disc, ring, web or other structure is sewn into the bowel from the inside. However, several additional approaches are covered in this application including clamping (pinch), suction, and friction.

Clamping Attachment

Figure 16:
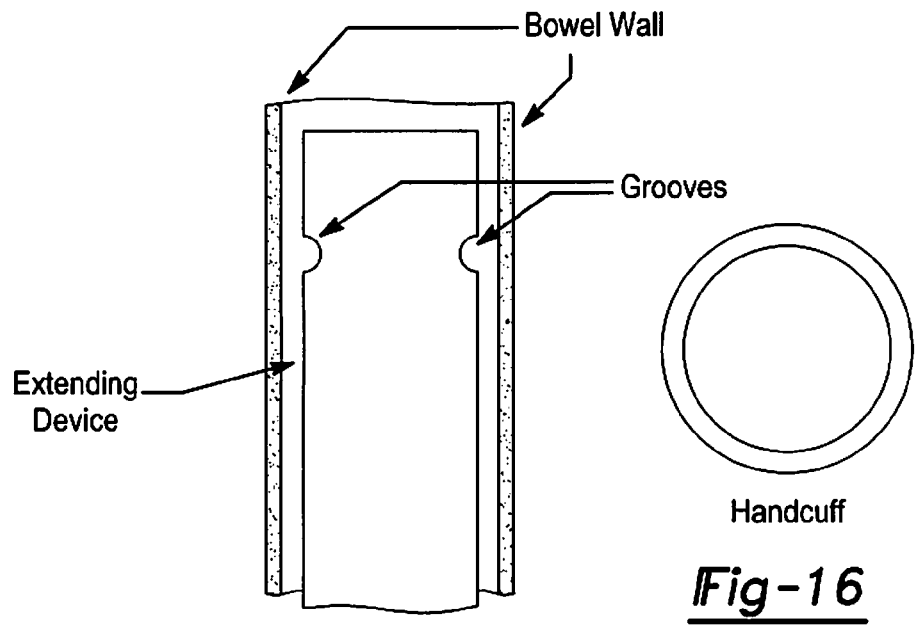
FIG. 16 illustrates a handcuff embodiment of a clamping attachment, where the handcuff mounts around the outside of the bowel clamping it against the groove of the implanted device.

The clamping approach shown in FIG. 16 employs a clamp from the outside of the bowel (like a hose clamp) which compresses the bowel wall against a portion of an internal device possibly against a groove. This has the advantage over sewn-in approaches of very evenly distributing the load along the whole circumference of the bowel which may produce more even (and therefore possibly better or faster) growth whereas attachment with force concentrations, at sutures, for example, may cause growth only near the stitch attachment points and may possibly damage the bowel at those location. Clamping attachment also has the advantage over end-abutting approaches in that it can be accomplished without removing the bowel segment from the continuity of the digestive tract, resulting in a less invasive surgery. This clamp approach could also be done magnetically, or with elastic bands, etc.

Suction Attachment

Figure 17:
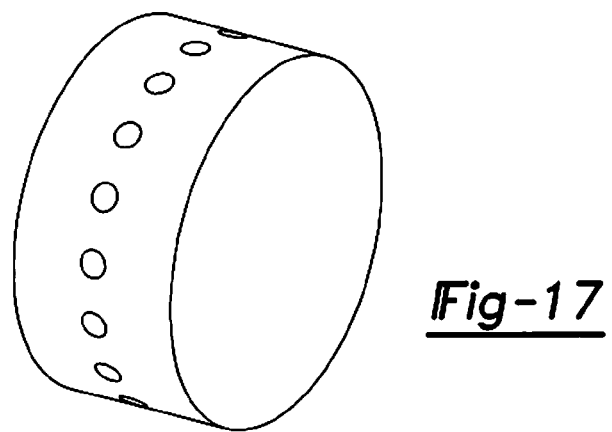
FIG. 17 illustrates a suction puck embodiment of a suction attachment, where suction is produced at the holes (by, for example, an SMA actuated bellows) around the disk's circumference, holding the bowel from the inside.

The suction approach to attachment employs suction around a ring to hold the bowel to an implanted device around its circumference. FIG. 17 shows a "suction puck" embodiment of this approach where suction is applied by a series of small holes around the circumference of a disk which is implanted within the bowel. Suction can be produced, for example, by building the puck with to rigid layers at the flat surfaces and a bellows between actuated by, for example, SMA wires. When the SMA wires contract, the bellows are compressed, expelling air from the circumferential holes. When the SMA wires relax, the bellows expand under their own elasticity, providing suction at the holes. Suction has all the advantages of the clamp approach with the additional advantage of not requiring any components outside the lumen of the bowel, improving patient safety and comfort, and possibly not requiring any surgery at all for insertion or removal. In addition, suction can be selectively engaged and disengaged after implantation, enabling other modalities of bowel extension which will be described later.

Friction Attachment

Rather than explicitly attach to the bowel wall, friction can be employed to produce a traction force from a device inside the bowel. A simple embodiment would be a device which has a large enough diameter at the ends to stretch the bowel circumferentially at those points, holding the bowel. Another embodiment would have radially expanding members at one or both ends to selectively engage and disengage the friction contact. Other embodiments could employ selective friction such as the fish scale concept shown in FIG. 18, where a directionally textured material provides high friction in one direction, producing tension, while enabling sliding in the other, enabling further modalities of bowel growth described later. Friction attachments have similar advantages to suction approaches with added simplicity of implementation, where directionally selective friction can be employed in a manner similar to selective suction.

New Classes of Bowel Expansion Methods

Previously, the only bowel growth modality used externally mounted devices—in particular, external screws. The present discussion discussed both segment-implanted lengthening devices and in-continuity implanted lengthening devices. New modalities are discussed in this document with distinct advantages over the previous modalities including paying-out approaches and track-following approaches.

Paying-Out Approaches

Rather than requiring the device to extend to the full length of the grown bowel segment as is by all the previously existing approaches, devices employing a paying-out approach maintain a relatively fixed length (possibly with small reciprocating longitudinal motions) applying tension to a fixed length of bowel, expelling the newly lengthened bowel off the end of the device as it grows. This motion can be incremental, where the device pulls on the bowel extending a small amount, allows growth, releases the bowel, retracts, and reattaches to the bowel, analogous to a person paying out length from a coiled rope, one arm's length at a time. Incremental paying out essentially acts as a ratchet, where the bowel itself plays a part of the ratchet mechanism itself. Alternatively, the motion can be continuous, analogous to extrusion processes in manufacturing. Paying out approaches have two very useful advantages: 1) one small device can grow bowel indefinitely, continuing to pay it out as it grows, and 2) no management of the path the bowel follows is necessary since the grown bowel is allowed to move and settle freely within the body cavity as it is paid out from the device.

Figure 18:
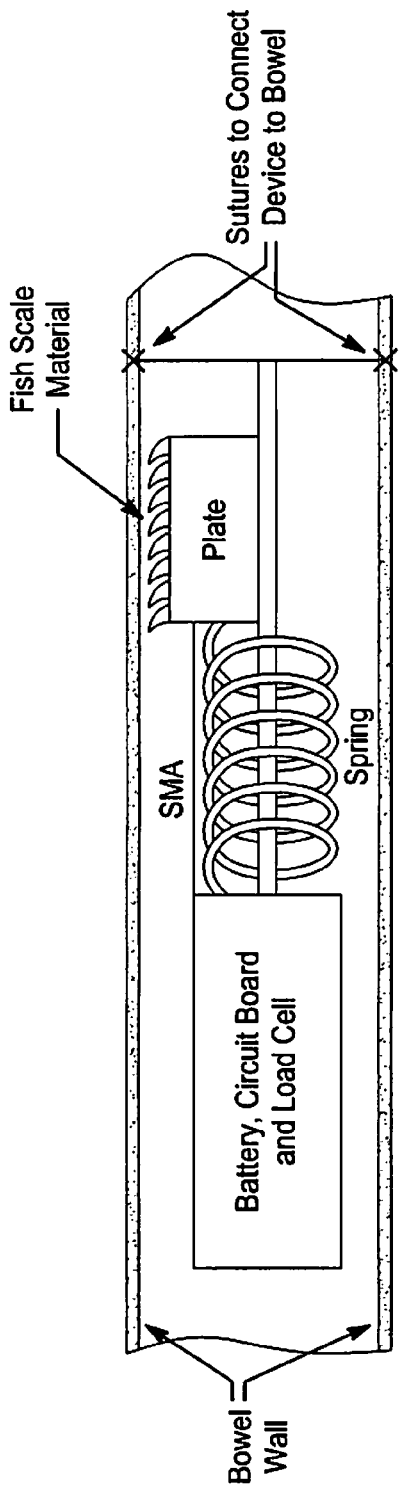
FIG. 18 illustrates a fish scale embodiment of a friction attachment, where directionally selective friction is produced by a series of scale-like surface features can push the bowel in one direction, producing tension, but allow free motion in the other.
Figure 19:
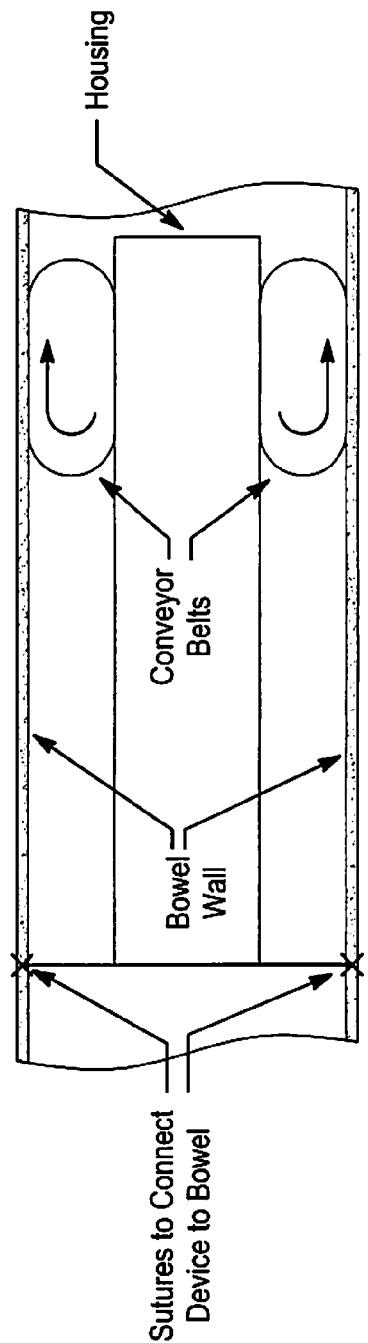
FIG. 19 illustrates a conveyor belt concept, where continuous paying out of the bowel is produced by traction developed by moving conveyor belts acting through friction on the bowel wall.

Embodiments of incremental paying may employ any attachment method that can be selectively disengaged, pulled back, and reengaged including the suction puck, fish-scale preferential friction as illustrated in FIG. 18 (which naturally engages and disengages without control or actuation), etc, where the incremental pull-back/push forward motion can be produced, for example, using an SMA wire—spring pair. One embodiment employing continuous paying out is the conveyor concept shown in FIG. 19, where one or more cyclic belts apply traction forces via friction to the bowel walls from the inside. These belts pull the bowel relative to the fixed end of the device and expel it off the free end as the bowel grows. The friction could be enhanced by the use of an external clamping collar in a hybrid attachment approach employing both clamping and friction methods. While many possibilities exist for actuating the conveyor belts in this embodiment, one possibility is to employ an SMA ratchet approach, shown in FIG. 20, where an SMA wire—spring pair produces a reciprocating motion which is transformed to a stepwise unidirectional motion of the belt through a directionally selective ratchet mechanism.

Track-Following Approaches

While the previously existing expansion approaches require the device to lengthen as the bowel grows, the track-following approach uses a track which is implanted in the bowel in continuity with a length and shape equal to that of the desired final growth of a smaller portion of the bowel. The bowel is attached at one end of the track and a track-following component starts along the track near the attached end. The bowel is attached to the track-following component defining the initial length of bowel between the track following and fixed end of the track, which is preferably short relative to the entire length of track. The track following component is then caused to travel along the track, applying tension to the initial length of bowel. The initial length of bowel grows, conforming to the shape of the track as the follower moves. The portion of the bowel initially over the track but not between the fixed end and the track-follower simply slides off the end of the track as the follower moves. The track can be as long as the entire length of existing bowel allows, while the initial length can be arbitrarily short. Since the track defines the shape of the growing bowel as the track-follower moves, complex curvilinear paths can be obtained. The track itself can be rigidly pre-shaped or even poseable to fit the particular patient's body cavity as shown in FIG. 21.

Alternatively the track can be compliant to conform to the body cavity while still guiding the growth of the bowel. Track following has several significant advantages over existing approaches: 1) it allows for much longer extension lengths within the geometric constraints of the body cavity. 2) It does it in a way that is much simpler mechanically than the more obvious approach of building a curved hydraulic piston or curved telescoping ratchet device, and 3) it allows customizable shape with many degrees of freedom which can be adapted to the configuration of a particular patient's bowel.

Figure 22:
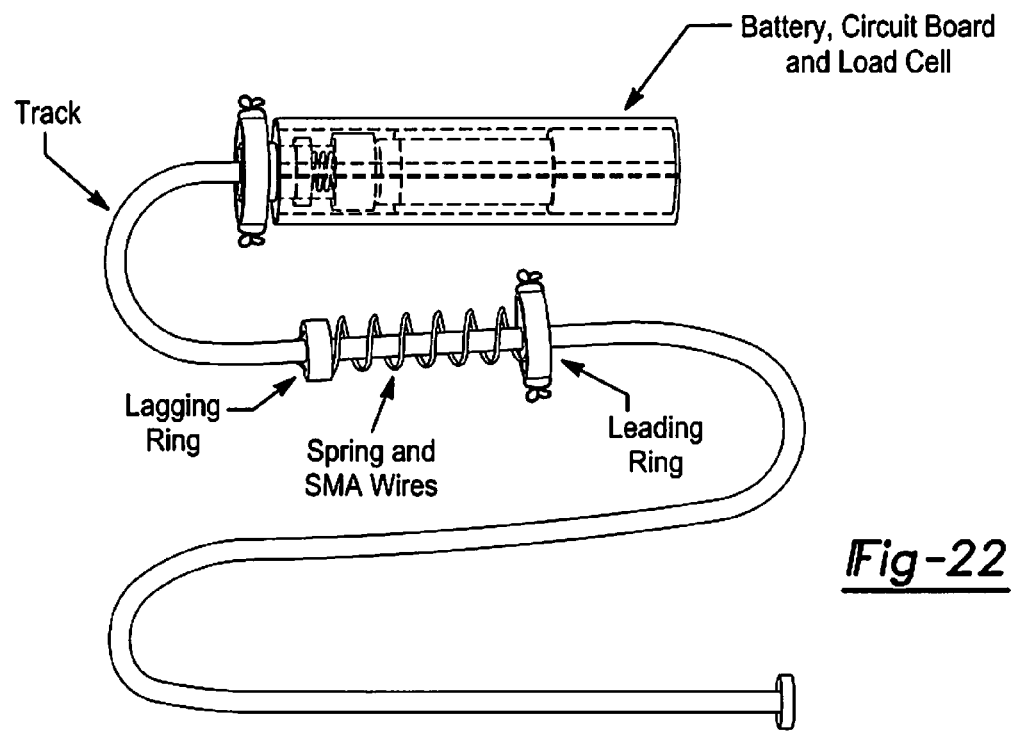
FIG. 22 illustrates an SMA ratchet track crawler, where an SMA-driven ratchet causes a crawler to incrementally moving along a track stretching the bowel over the length of the track.
Figure 23:
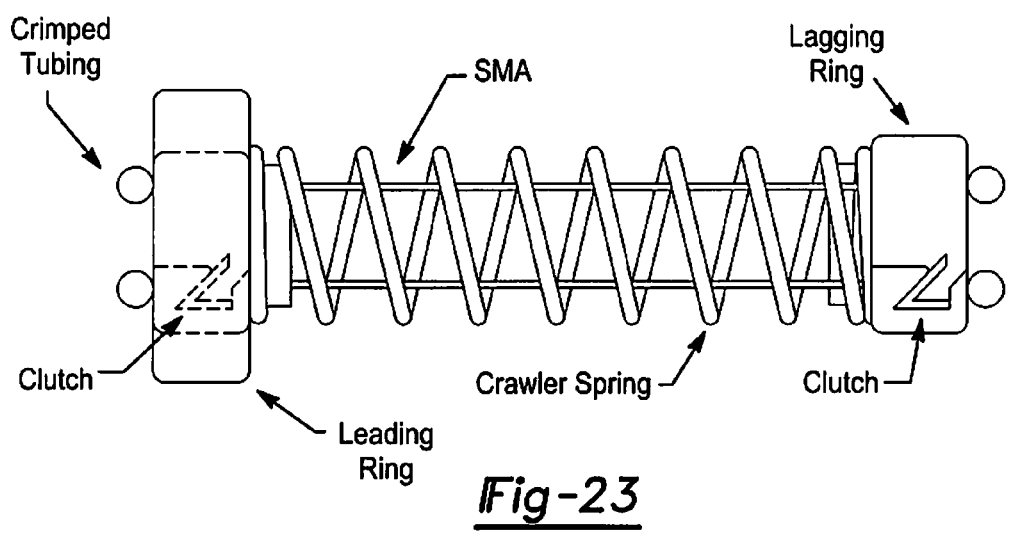
FIG. 23 illustrates details of crawler, where ratchet flaps allow motion only forward along the track enabling ratcheting driven by the SMA wire/spring pair.
Figure 24:
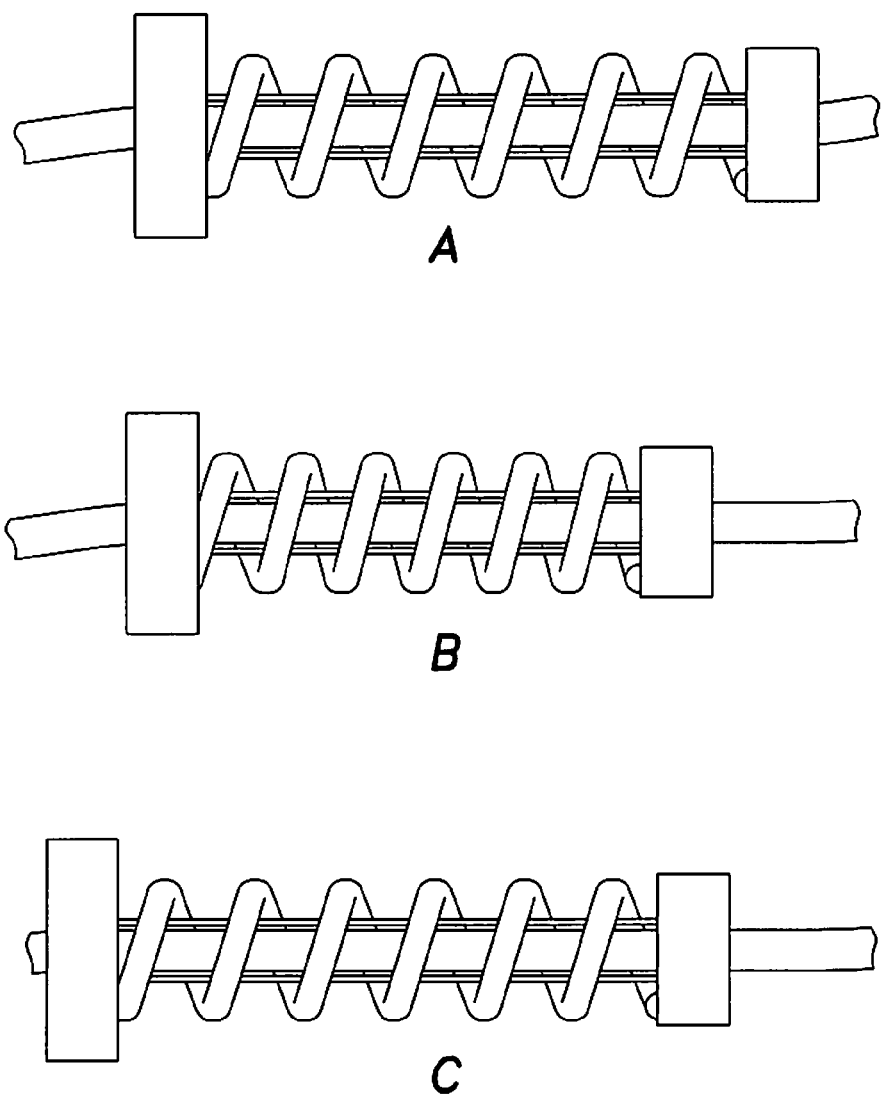
FIG. 24 illustrates the ratcheting operation of the crawler, where reciprocating motion of the SMA-spring pair produces incremental forward (leftward) motion of the crawler along the track.
Figure 25:
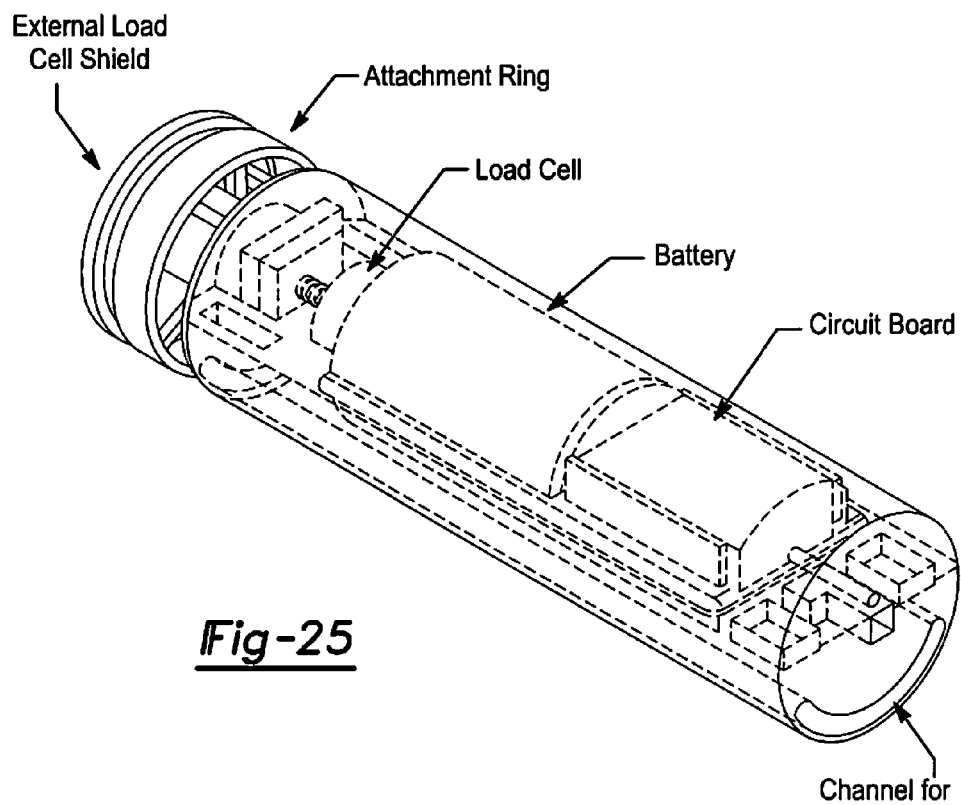
FIG. 25 illustrates the SMA ratchet track crawler housing, where the track crawler is implanted in continuity with the bowel, and therefore must have channels and holes through which fluids may flow.
Figure 26:
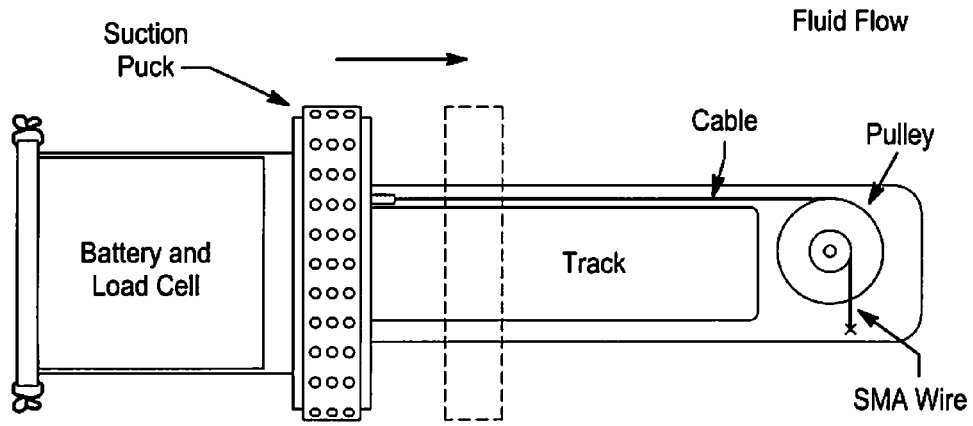
FIG. 26 illustrates the SMA ratchet track crawler housing, where the track crawler is implanted in continuity with the bowel, and therefore must have channels and holes through which fluids may flow.

One embodiment of track-following employs a crawler based on an SMA-driven ratchet to move along the track as shown in FIG. 21. The bowel is attached at the front (as shown or alternatively the back) end of the main body of the device containing the power, sensing, and control components and at the leading ring of the crawler assembly. In this embodiment, directional ratchet flaps (clutches) within the leading and lagging rings of the crawler assembly (FIG. 22) allow each ring to move only in the forward direction along the track. When the SMA wire contracts, the lagging ring is pulled forward along the track by one step. When the SMA wire relaxes, the return spring pushes the leading track forward one step (FIG. 24). The assembly can negotiate the curved track because the spring itself, concentric with the track, provides a bendable connection between the two rings. Since the entire device is implanted in the bowel, each component must have channels or holes through which fluids can flow (FIG. 26).

Another embodiment of track following uses the entire length of track as a rigid compression member, where a flexible element such as a cord or cable pulls the track-following element along the track. FIG. 26 shows an example of this embodiment where an SMA driven pulley at the free end of the track winds in a cable which pulls a suction puck (which could be replaced by a movable component employing any attachment method) along the track. Note that while the figure shows a short straight track, a long curved track is made possible by guiding the cable along curves of the track through a slot or series of rings attached to the track. Another modality for such a device in the case of a selectively engagable attachment such as the suction puck or fish-scale preferential friction is to pull the movable element along the track, disengage the attachment, pull the movable element back to the beginning of the track using, for example, a bias spring or second cable, reattaching, and repeating the process. This forms a hybrid approach between paying out and track-following, enabling very large and rapid growth.

New Motion Generation Methods

Within any class of bowel extension, many methods exist for actually producing the requisite motion. The embodiments discussed herein employing fluidic (hydraulic) and ratcheting (via SMA wires, for example) methods can be used. However, additional methods for generating motion for bowel extension devices including passive motion and distributed mechanism can be used.

Passive Motion Generation

Motion can be developed using a passive spring-like element rather than an actively actuated element such as SMA or a hydraulic piston. Such methods start with a compliant structure compressed (or stretched in an alternate mode of operation) to an initial length, implanted within the bowel attached at each end, and then allowed to expand over time, applying tension to the bowel as the bowel grows. Passive motion can be uncontrolled where the tensile force is determined by the current length of the device, and the extension rate is determined by the growth reaction of the bowel. Alternatively, the motion can be regulated where the spring is allowed to expand as determined by an actively controlled mechanism. The compliant member can be any axially compressible structure, so a coil spring, a webbing of foil, an accordion-like structure, etc, and can be made of traditional materials (metal, plastic, etc) or alternatively, shape memory alloy working in superelastic mode (for example).

Figure 27:
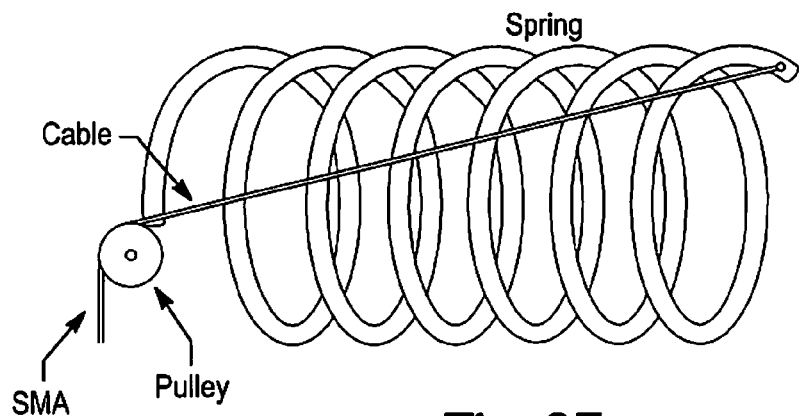
FIG. 27 illustrates the cable-driven passive expander, where an SMA-driven pulley unwinds a cable winch which allows a spring to expand and apply tensile forces to the bowel.

FIG. 27 shows a coiled spring which is payed out over time to effect extension motion. While the paying out device is actuated in this embodiment, the actual motion generated is entirely passive, and thus fundamentally different than our existing IP. This has the great advantage of being much simpler mechanically. Passive motion can be either payed out in a controlled way, like the embodiment shown, or it can be entirely uncontrolled where a compliant member is compressed (like a snake in a can) inside a bowel segment and the rate of expansion is entirely determined by the match between the force-deflection properties designed into the compliant member and the growth response to these forces of the bowel. The compliant member can be any axially compressible structure, so a coil spring, a webbing of foil, an accordion-like structure, etc, and can be made of traditional materials (metal, plastic, etc) or shape memory alloy working in superelastic mode (for example). Such methods have the great advantage of being mechanically very simple and, depending on the control method, require little or no power to produce motion. They also can work well in an in-continuity mode since it is straightforward to construct a compliant element through which fluids may flow.

One embodiment of a passive expander is shown in FIG. 27, where a coil spring is allowed to expand as determined by a cable inside the spring. The cable is wound on a pulley which is allowed to rotate by, for example, an SMA wire actuator. Note that the spring in this case can be inserted freely in the body, operating in a (segment or in-continuity) lengthening device mode, or can be installed over a curved track, operating in a track-following mode for enhanced expansion within the confines of the body cavity. Note that the use of a track enables an even simpler approach using, for example, an elastic band to pull the bowel along the track rather than a spring to push along it. The band can be looped over the end of the track and back again to provide expansion along the full length of track. Many options exist for actuating the mechanism which allows the cable to unwind including a fully-passive spring-escapement mechanism which is wound up like a watch before implantation allowing the main extension spring to expand in a regulated manner, requiring no power at all.

Figure 28:
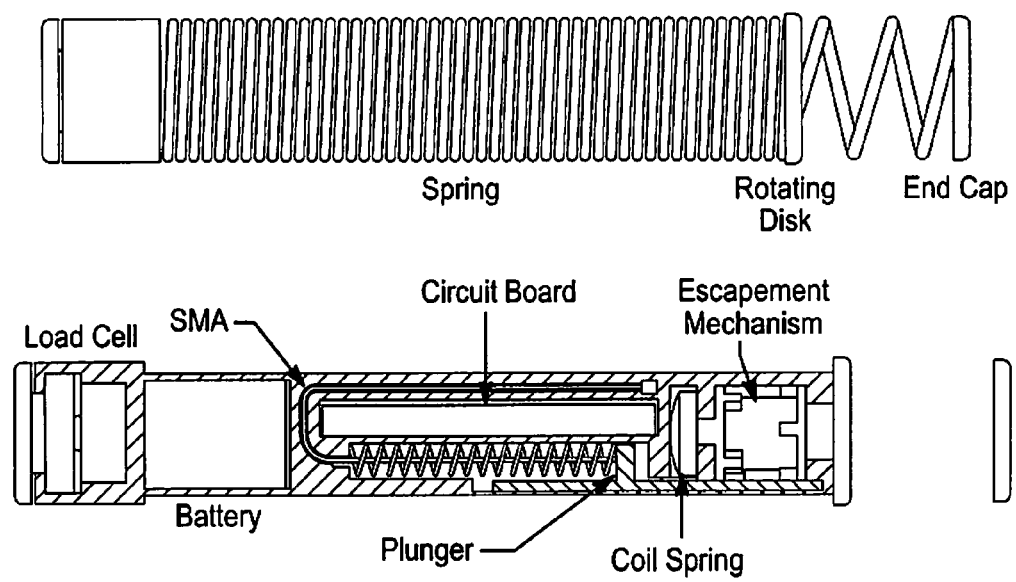
FIG. 28 illustrates the rotating-disc spring expander, where a spring is allowed to expand as a disc through which it is threaded rotates as allowed by an SMA driven spring-escapement mechanism.

Another embodiment of a passive expander is shown in FIG. 28. This rotating-disk spring concept uses a spring which is compressed and held around a cylinder (also containing other components for power, sensing, and control). A rotating disk with an angled hole to allow passage of the spring wire is placed on one end of the cylinder. The spring threads through this disk and connects to an end cap. When the disk rotates, the spring is let out through the hole in the disk, which will apply a load to the end cap and, thus, the bowel. This disk is connected to a coil spring so that a moment is constantly applied to the disk. An SMA wire is connected to a plunger inside an escapement mechanism. Heating the SMA causes the wire to contract and when the wire cools the spring forces it back to its original position. When these motions of the tab are accomplished, the rotating disk is allowed to spin in small increments, thus releasing the spring and applying a load on the bowel as shown in FIG. 29.

Distributed Mechanism

Motion for bowel extension can be generated through the use of a distributed mechanism which leverages motion from the actuator throughout the entire length of the device as it expands. Many different jointed, compliant, and rotary linkages are possible to distribute the motion along the length, for example, a series of scissor mechanisms (like fireplace tongs or the comic boxing glove) with an SMA wire actuator at one end, where all portions ove the length of the device expand. An alternative approach also employs distributed actuation throughout the mechanism where each of a series of actuators induces extension locally and their combined motion produces a bulk lengthening of the device. These actuators can be all activated together a small amount at a time, or each actuator can be fully activated one at a time to incrementally expand the device. An embodiment of such an approach is shown in FIG. 30, where SMA wire segments mounted at each jointed segment of a decoupled series scissor mechanism expand each segment one at a time. Note that the distributed mechanism in this case can be inserted freely in the body, operating in a (segment or in-continuity) lengthening device mode, or can be installed over a curved track, operating in a track-following mode for enhanced expansion within the confines of the body cavity. Also, passive expansion can be employed at each joint, with discrete springs, for example, or even compliant joints which naturally expand. In this latter hybrid between passive expansion and distributed mechanism, the motion can be incrementally controlled with (SMA actuated, for example) release latches which can allow each segment to expand out in series, thereby controlling the expansion.

What is claimed is:

1. A bowel extension device for implantation into the lumen of the bowel of a body, said bowel extension device comprising:
   a housing defining an outer dimension that is less than an inner dimension of the bowel such that enteric contents within the bowel can flow past said housing;
   a displaceable member movably coupled to said housing; and
   an actuation system moving said displaceable member from a retracted position to an extended position to apply a tensile force sufficient to promote bowel growth without causing damage to the bowel such that said bowel growth is urged beyond the length of the bowel extension device,
   at least one of said housing and said displaceable member includes a textured surface frictionally engageable with the lumen, said actuation system having:
   a movable collar,
   a Shape Memory Alloy (SMA) wire coupling said movable collar and said displaceable member,
   a ratchet system operably extending between said movable collar and said displaceable member preventing retraction of said movable collar relative to said displaceable member, and
   a spring member opposing said Shape Memory Alloy wire,
   wherein said housing and said displaceable member are configured to be disposed within said bowel of a body after implantation of said bowel extension device, wherein only one of said housing and said displaceable member is adapted to be fixedly coupled to the lumen of said bowel at a first end of the bowel extension device such that said bowel growth is urged beyond an opposing second end of the bowel extension device, and
   wherein said actuation system moving said displaceable member from a retracted position to an extended position is reciprocal in nature such that said bowel growth is incrementally urged beyond the length of the bowel extension device, an overall length of said bowel extension device alternating as said actuation system moves from said retracted position to said extended position.

2. The bowel extension device according to claim 1 wherein at least a portion of said housing or displaceable member is adapted to extend within a stomach of the body.

3. The bowel extension device according to claim 1 wherein the other of said only one of said housing and said displaceable member is adapted to be selectively coupled to the lumen such that as said actuation system is reciprocally actuated between said retracted position and said extended position, said coupling to the lumens is achieved during movement toward said extended position and said decoupling from the lumens is achieved during movement toward said retracted position.

4. The bowel extension device according to claim 1 wherein the other of said only one of said housing and said displaceable member is adapted to be selectively coupled to the lumen such that as said actuation system is actuated into said retracted position and decoupled from the lumen and as said actuation system is actuated into said extended position, said selective coupling to the lumen applies said tensile force sufficient to promote bowel growth urged beyond the length of the bowel extension device.

5. The bowel extension device according to claim 1 wherein the other of said only one of said housing and said displaceable member is adapted to be selectively coupled to the lumen such that as said actuation system is reciprocally actuated, said bowel extension device is inserted into or removed from the bowel.

6. The bowel extension device according to claim 1 wherein said textured surface comprises a textured surface having directionally-dependent friction such that said at least one of said housing and said displaceable member is frictionally attachable with the lumen in a first direction and detachable from the lumen in a second direction.

7. The bowel extension device according to claim 1 wherein the other of said only one of said housing and said displaceable member is selectively attachable to the lumen using retractable teeth, said retractable teeth being moveable between an extended position and a retracted position.

8. The bowel extension device according to claim 1 wherein the other of said only one of said housing and said displaceable member is selectively attachable to the lumen using an expandable element selectively applying an outward force to frictionally engage the lumen when expanded.

* * * * *